US008945888B2

(12) United States Patent
Dischert et al.

(10) Patent No.: US 8,945,888 B2
(45) Date of Patent: Feb. 3, 2015

(54) METHOD FOR PRODUCING HIGH AMOUNT OF GLYCOLIC ACID BY FERMENTATION

(75) Inventors: Wanda Dischert, Vic-le-Comte (FR); Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 542 days.

(21) Appl. No.: 13/258,366

(22) PCT Filed: Mar. 23, 2010

(86) PCT No.: PCT/EP2010/053758
§ 371 (c)(1),
(2), (4) Date: Dec. 7, 2011

(87) PCT Pub. No.: WO2010/108909
PCT Pub. Date: Sep. 30, 2010

(65) Prior Publication Data
US 2012/0315682 A1  Dec. 13, 2012

Related U.S. Application Data

(60) Provisional application No. 61/162,712, filed on Mar. 24, 2009.

(30) Foreign Application Priority Data

Mar. 24, 2009  (EP) .................................... 09155971

(51) Int. Cl.
| | |
|---|---|
| *C12P 7/42* | (2006.01) |
| *C12N 9/00* | (2006.01) |
| *C12N 1/20* | (2006.01) |
| *C12N 15/00* | (2006.01) |
| *C07H 21/04* | (2006.01) |
| *C12N 9/04* | (2006.01) |
| *C12N 9/88* | (2006.01) |

(52) U.S. Cl.
CPC ................ *C12P 7/42* (2013.01); *C12N 9/0006* (2013.01); *C12N 9/88* (2013.01)
USPC ..... 435/146; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 7,700,332 B1 | 4/2010 | Rajgarhia et al. | |
| 2006/0073577 A1 | 4/2006 | Ka-Yiu et al. | |
| 2009/0155867 A1 | 6/2009 | Soucaille | |
| 2010/0261239 A1 | 10/2010 | Soucaille et al. | |
| 2010/0285547 A1 | 11/2010 | Soucaille et al. | |

FOREIGN PATENT DOCUMENTS

| | | |
|---|---|---|
| EP | 1382686 | 1/2004 |
| WO | 2004/033646 | 4/2004 |
| WO | 2006/020663 | 2/2006 |
| WO | 2006/034156 | 3/2006 |
| WO | 2007/140816 | 12/2007 |
| WO | 2007/141316 | 12/2007 |
| WO | 2008/013405 | 1/2008 |
| WO | 2008/116848 | 10/2008 |
| WO | 2008/116852 | 10/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Seffernick et al. J Bacteriol. Apr. 2001; 183 (8): 2405-10.*
Witkowski et al. Biochemistry. Sep. 7, 1999; 38(36): 11643-50.*
International Search Report for PCT/EP2010/053758 Mailed Jul. 6, 2010.
European Search Report Based on EP 09 15 5971 Search Completed Jun. 8, 2009; 3 Pgs.
Alexeeva et al.; "Requirement of ArcA for Redox Regulation in *Escherichia coli* Under Microaerobic But Not Anaerobic or Aerobic Conditions"; Journal of Bacteriology; Jan. 2003; pp. 204-209; vol. 185; No. 1; American Society for Microbiology.
Anderson; "Growth Requirements of Virus-Resistant Mutants of *Escherichia coli* Strain "B""; Proc. N. A. S.; 1946; pp. 121-128; vol. 32.
Bauer et al.; "Mechanisms for Redox Control of Gene Expression"; Annu. Rev. Microbiol.; 1999; pp. 495-523; vol. 53; Annual Reviews.
Carrier et al.; "Library of Synthetic 5' Secondary Structures to Manipulate MRNA Stability in *Escherichia coli*"; Biotechnol. Prog.; 1999; pp. 58-64; vol. 15; American Society and American Institute of Chemical Engineers.
Cozzone et al.; "Control of Isocitrate Dehydrogenase Catalytic Activity by Protein Phosphorylation in *Escherichia coli*"; J. Mol. Microbiol Biotechnol; 2005; pp. 132-146; vol. 9. S. Krager AG. Basel.
Datsenko et al.; "One-Step Inactivation of Chromosomal Genes in *Escherichia coli* K-12 Using PCR Products"; PNAS; Jun. 6, 2000; pp. 6640-6645; vol. 97; No. 12.
Georgellis et al.; "Amplification of Signaling Activity of the Arc Two-Component System of *Escherichia coli* by Anaerobic Metabolites"; The Journal of Biological Chemistry; Dec. 10, 1999; pp. 35950-35954; vol. 274, No. 50; American Society for Biochemistry and Molecular Biology, Inc.
Gimenez et al.; "The Gene YJCG, Cotranscribed With the Gene ACS, Encodes an Acetate Permease in *Escherichia coli*"; Journal of Bacteriology; Nov. 2003; pp. 6448-6455; vol. 185; No. 21; American Society for Microbiology.
Ikeda et al.; "Isocitrate Dehydrogenase Kinase/Phosphatase: Identification of Mutations Which Selectively Inhibit Phosphatase Activity"; Journal of Bacteriology; Feb. 1992; pp. 1414-1416; vol. 174; No. 4; American Society for Microbiology.

(Continued)

*Primary Examiner* — Christian Fronda
(74) *Attorney, Agent, or Firm* — Miles & Stockbridge P.C.

(57) ABSTRACT

The present invention relates to an improved method for the bioconversion of a fermentable carbon source to glycolic acid by a recombinant microorganism bearing new genetic modifications such as ΔldhA, ΔmgsA, ΔarcA, and ΔlldP, ΔglcA, ΔyjcG and combination of them allowing a production with higher yield, titer and productivity.

19 Claims, 3 Drawing Sheets

(56) References Cited

OTHER PUBLICATIONS

Iuchi et al.; "Adaptation of *Escherichia coli* to Respiratory Conditions: Regulation of Gene Expression"; Cell; Jul. 12, 1991; pp. 5-7; vol. 66; No. 1; Cell Press.

Iuchi et al.; "Adaptation of *Escherichia coli* to Redox Environments by Gene Expression"; Molecular Microbiology; 1993; vol. 9.; No. 1; pp. 9-15.

Iuchi et al.; "ArcA (DYE), A Global Regulatory Gene in *Escherichia coli* Mediating Repression of Enzymes in Aerobic Pathways"; Proc. Natl. Acad. Sci.; Mar. 1988; pp. 1888-1892; vol. 85; Genetics.

Jeong et al.; "Expression of PTSG Encoding the Major Glucose Transporter Is Regulated by ArcA in *Escherichia coli*"; The Journal of Biological Chemistry; Sep. 10, 2004; pp. 38513-38518; vol. 279; No. 37; The American Society for Biochemistry and Molecular Biology, Inc.

Laporte et al.; "Isocitrate Dehydrogenase Kinase/Phosphatase"; Biochemie; 1989; pp. 1051-1057; vol. 71; Societe De Chemie Biologique/Elsevier, Paris.

Laub et al.; "Specificity in Two-Component Signal Transduction Pathways"; Annu. Rev. Genet.; 2007; pp. 121-145; vol. 41; Annual Reviews.

Liu et al.; "Probing the ArcA-P Modulon of *Escherichia coli* by Whole Genome Transcriptional Analysis and Sequence Recognition Profiling"; The Journal of Biological Chemistry; Mar. 26, 2004; pp. 12588-12597; vol. 279; No. 13; The American Society for Biochemistry and Molecular Biology, Inc.; The American Society.

Nunez et al.; "Biochemical Characterization of the 2-Ketoacid Reductases Encoded by ycdW and YIAE Genes in *Escherichia coli*"; Biochem. J.; 2001; pp. 707-715; vol. 354; Biochemical Society.

Nunez et al.; "The Gene YGHK Linked to the GLC Operon of *Escherichia coli* Encodes a Permease for Glycolate That Is Structurally and Functionally Similar to L-Lactate Permease"; Microbiology; Apr. 9, 2001; pp. 1067-1077; vol. 147; SGM.

Nunez et al.; "Transport of L-Lactate, D-Lactate, and Glycolate by the lidP and glcA Membrane Carriers of *Escherichia coli*"; Biochemical and Biophysical Research Communications; 2002; pp. 824-829; vol. 290; Elsevier Science; INIST CNRS (2006).

Palmeros et al.; A Family of Removable Cassettes Designed to Obtain Antibiotic-Resistance-Free Genomic Modifications of *Escherichia coli* and Other Bacteria; Gene; 2000; pp. 255-264; vol. 247; Elseivier Science B.V.

Perrenoud et al.; "Impact of Global Transcriptional Regulation by ArcA, ArcB, CRA, CRP, CYA, FNR, and MLC on Glucose Catabolism in *Escherichia coli*"; Journal of Bacteriology; May 2005; pp. 3171-3179; vol. 187; No. 9; American Society for Microbiology.

Shalel-Levanon et al.; "Effect of Oxygen on the *Escherichia coli* ArcA and FNR Regulation Systems and Metabolic Responses"; Biotechnology and Bioengineering; vol. 89; No. 5; Mar. 2005; pp. 556-564; Wiley Periodicals, Inc.

Shalel-Levanon et al.; "Effect of ArcA and FNR on the Expression of Genes Related to the Oxygen Regulation and the Glycolysis Pathway in *Escherichia coli* Under Microaerobic Growth Conditions"; Biotechnology and Bioengineering; Oct. 20, 2005; pp. 147-159; vol. 92; No. 2; Wiley Periodicals, Inc.

Cozzone; "Regulation of Acetate Metabolism by Protein Phosphorylation in Enteric Bacteria"; Annu. Rev. Microbiol.; 1998; pp. 127-164; vol. 52; Annual Reviews.

Hansen et al.; "Simple Downshift and Resulting Lack of Correlation Between PPGPP Pool Size and Ribonucleic Acid Accumulation"; Journal of Bacteriology; May 1975; pp. 585-591; vol. 122; No. 2; American Society for Microbiology.

Nishigami et al.; "Growth Inhibition by D-Mannosamine and Its Reversal by Glucose and Mannose in *Bacillus subtilis*"; Plant & Cell Physiol.; 1984; pp. 657-664; vol. 25; No. 4; JSPP.

Sanchez et al.; "Batch Culture Characterization and Metabolic Flux Analysis of Succinate-Producing *Escherichia coli* Strains"; Metabolic Engineering; 2006; pp. 209-226; vol. 8; Elsevier Inc (2005).

Wendisch et al.; "Metabolic Engineering of *Escherichia coli* and *Corynebacterium glutamicum* for Biotechnological Production of Organic Acids and Amino Acids"; Current Opinion in Microbiology; 2006; pp. 268-274; vol. 9; Elsevier.

Lynch et al.; "Responses to Molecular Oxygen"; *Escherichia coli* and *Salmonella*: Cellular and Molecular Biology; Second Edition; pp. 1526-1538; vol. 1; 1996; ASM Press.

Neidhardt et al.; *Escherichia coli* and *Salmonella*: Cellular and Molecular Biology; 1996; American Society for Microbiology.

Sambrook et al.; Molecular Cloning: A Laboratory Manual. 2nd Edition; Cold Spring Harbor Lab.; Cold Spring Harbor, New York.

\* cited by examiner

SEQUENCE LISTING

<160> NUMBER OF SEQ ID NOS: 34

<210> SEQ ID NO 1
<211> LENGTH: 119
<212> TYPE: DNA
<213> ORGANISM: Artificial sequence
<220> FEATURE:
<223> OTHER INFORMATION: Oligonucleotide

<400> SEQUENCE: 1

```
ggacgcaaac gcatatgcaa cgtggtggca gacgagcaaa ccagtagcgc tcgaaggaga    60
ggtgatcaca ctggctcacc ttcgggtggg cctttctgcc atatgaatat cctccttag   119
```

<210> SEQ ID NO 2
<211> LENGTH: 134
<212> TYPE: DNA
<213> ORGANISM: Artificial sequence
<220> FEATURE:
<223> OTHER INFORMATION: Oligonucleotide

<400> SEQUENCE: 2

```
gccgttttgc agggtgatct tcttgccttg tgccggaaca actactttac tttccaaagc    60
tgtttccttc ttaccacaca gtatacgagc cggatgatta atcgccaaca gctctgtagg   120
ctggagctgc ttcg                                                     134
```

<210> SEQ ID NO 3
<211> LENGTH: 100
<212> TYPE: DNA
<213> ORGANISM: Artificial sequence
<220> FEATURE:
<223> OTHER INFORMATION: Oligonucleotide

<400> SEQUENCE: 3
gaaactcgcc gtttatagca caaaacagta cgacaagaag tacctgcaac aggtgaacga    60
gtcctttggc tttgagctgg tgtaggctgg agctgcttcg                         100

<210> SEQ ID NO 4
<211> LENGTH: 101
<212> TYPE: DNA
<213> ORGANISM: Artificial sequence
<220> FEATURE:
<223> OTHER INFORMATION: Oligonucleotide

<400> SEQUENCE: 4
ttaaaccagt tcgttcgggc aggtttcgcc tttttccaga ttgcttaagt tttgcagcgt    60
agtctgagaa atactggtca gcatatgaat atcctcctta g                       101

<210> SEQ ID NO 5
<211> LENGTH: 100
<212> TYPE: DNA
<213> ORGANISM: Artificial sequence
<220> FEATURE:
<223> OTHER INFORMATION: Oligonucleotide

<400> SEQUENCE: 5
gcaggctttt tcggtcttta tcttgcagcg ataagtgctt acagtaatct gtaggaaagt    60
taactacgga tgattccggg gatccgtcga cctgcagttc                         100

<210> SEQ ID NO 6
<211> LENGTH: 100
<212> TYPE: DNA
<213> ORGANISM: Artificial sequence
<220> FEATURE:
<223> OTHER INFORMATION: Oligonucleotide

<400> SEQUENCE: 6
ggatgtgccg gtggcgagaa aaccgtaaga aacaggtggc gtttgccacc tgtgcaatat    60
tacttcagac ggtccgcgag tgtaggctgg agctgcttcg                         100

<210> SEQ ID NO 7
<211> LENGTH: 101
<212> TYPE: DNA
<213> ORGANISM: Artificial sequence
<220> FEATURE:
<223> OTHER INFORMATION: Oligonucleotide

<400> SEQUENCE: 7
gtaatctgta ggaaagttaa ctacggatgt acattatgga actgacgact cgcactttac    60
ctgcgcggaa acatattgcg ccatatgaat atcctcctta g                       101

<210> SEQ ID NO 8
<211> LENGTH: 100
<212> TYPE: DNA
<213> ORGANISM: Artificial sequence
<220> FEATURE:
<223> OTHER INFORMATION: Oligonucleotide

<400> SEQUENCE: 8
ggcgtttgcc acctgtgcaa tattacttca gacggtccgc gagataacgc tgataatcgg    60
ggatcagaat atcgaccgcg tgtaggctgg agctgcttcg                         100

```
<210> SEQ ID NO 9
<211> LENGTH: 98
<212> TYPE: DNA
<213> ORGANISM: Artificial sequence
<220> FEATURE:
<223> OTHER INFORMATION: Oligonucleotide

<400> SEQUENCE: 9
ccccgcacat tcttatcgtt gaagacgagt tggtaacacg caacacgttg aaaagtattt      60
tcgaagcgga aggctatgtg taggctggag ctgcttcg                              98

<210> SEQ ID NO 10
<211> LENGTH: 99
<212> TYPE: DNA
<213> ORGANISM: Artificial sequence
<220> FEATURE:
<223> OTHER INFORMATION: Oligonucleotide

<400> SEQUENCE: 10
ccagatcacc gcagaagcga taaccttcac cgtgaatggt ggcgatgatt tccggcgtat      60
ccggcgtaga ttcgaaatgc atatgaatat cctccttag                             99

<210> SEQ ID NO 11
<211> LENGTH: 99
<212> TYPE: DNA
<213> ORGANISM: Artificial sequence
<220> FEATURE:
<223> OTHER INFORMATION: Oligonucleotide

<400> SEQUENCE: 11
ggttacctgg acccaaatgt atatgccgat gggaggactg gggctatccg ctctggtcgc      60
cctgatcccg ataatattca attaaccctc actaaggg                              99

<210> SEQ ID NO 12
<211> LENGTH: 99
<212> TYPE: DNA
<213> ORGANISM: Artificial sequence
<220> FEATURE:
<223> OTHER INFORMATION: Oligonucleotide

<400> SEQUENCE: 12
cgagactaac atcccggtaa acacatacgc ctgcagcagg gtgataatgc cgataacgct      60
ggcaaaaatc agactgtgct aatacgactc actataggg                             99

<210> SEQ ID NO 13
<211> LENGTH: 100
<212> TYPE: DNA
<213> ORGANISM: Artificial sequence
<220> FEATURE:
<223> OTHER INFORMATION: Oligonucleotide

<400> SEQUENCE: 13
gacctgcaat gaatctctgg caacaaaact acgatcccgc cgggaatatc tggctttcca      60
gtctgatagc atcgcttccc catatgaata tcctccttag                            100

<210> SEQ ID NO 14
<211> LENGTH: 99
<212> TYPE: DNA
<213> ORGANISM: Artificial sequence
<220> FEATURE:
<223> OTHER INFORMATION: Oligonucleotide
```

-continued

<400> SEQUENCE: 14
cataagcctg aagcgtggtg atcacgccca ctatacaggt gaagatcagg ctgtgtttga    60
cagtaaagcg gaacaaatct gtaggctgga gctgcttcg                          99

<210> SEQ ID NO 15
<211> LENGTH: 100
<212> TYPE: DNA
<213> ORGANISM: Artificial sequence
<220> FEATURE:
<223> OTHER INFORMATION: Oligonucleotide

<400> SEQUENCE: 15
gttctgacgg cgcttgccgc cacactccct ttcgcagcta acgccgcgga tgctattagc    60
ggggccgtag agcgccagcc aattaaccct cactaaaggg                         100

<210> SEQ ID NO 16
<211> LENGTH: 99
<212> TYPE: DNA
<213> ORGANISM: Artificial sequence
<220> FEATURE:
<223> OTHER INFORMATION: Oligonucleotide

<400> SEQUENCE: 16
gcgcgcggcc ttgctcaacg ccaaagccgg tctgggagcg gataaactgc gcgcggaaca    60
gttcacgctc acgcgcgcct aatacgactc actatagggg                         99

<210> SEQ ID NO 17
<211> LENGTH: 35
<212> TYPE: DNA
<213> ORGANISM: Artificial sequence
<220> FEATURE:
<223> OTHER INFORMATION: Oligonucleotide

<400> SEQUENCE: 17
cctaccggta tgggcgagca aatgcaggaa tatgc                              35

<210> SEQ ID NO 18
<211> LENGTH: 86
<212> TYPE: DNA
<213> ORGANISM: Artificial sequence
<220> FEATURE:
<223> OTHER INFORMATION: Oligonucleotide

<400> SEQUENCE: 18
gcatgcatcc cggggcagaa aggcccaccc gaaggtgagc cagtgtgaag atctttagta    60
gccgcgtgcg cggtcgactt gcccgc                                        86

<210> SEQ ID NO 19
<211> LENGTH: 32
<212> TYPE: DNA
<213> ORGANISM: Artificial sequence
<220> FEATURE:
<223> OTHER INFORMATION: Oligonucleotide

<400> SEQUENCE: 19
cccaagcttc atattgttat caacaagtta tc                                 32

<210> SEQ ID NO 20
<211> LENGTH: 29
<212> TYPE: DNA
<213> ORGANISM: Artificial sequence
<220> FEATURE:
<223> OTHER INFORMATION: Oligonucleotide

```
<400> SEQUENCE: 20
tcccccgggg cttagaactg cgattcttc                                    29

<210> SEQ ID NO 21
<211> LENGTH: 21
<212> TYPE: DNA
<213> ORGANISM: Artificial sequence
<220> FEATURE:
<223> OTHER INFORMATION: Oligonucleotide

<400> SEQUENCE: 21
cagagattat gaattgccgc a                                            21

<210> SEQ ID NO 22
<211> LENGTH: 21
<212> TYPE: DNA
<213> ORGANISM: Artificial sequence
<220> FEATURE:
<223> OTHER INFORMATION: Oligonucleotide

<400> SEQUENCE: 22
ccaggagatt ttacgctcgc c                                            21

<210> SEQ ID NO 23
<211> LENGTH: 20
<212> TYPE: DNA
<213> ORGANISM: Artificial sequence
<220> FEATURE:
<223> OTHER INFORMATION: Oligonucleotide

<400> SEQUENCE: 23
gccatcagca ggcttagcgc                                              20

<210> SEQ ID NO 24
<211> LENGTH: 23
<212> TYPE: DNA
<213> ORGANISM: Artificial sequence
<220> FEATURE:
<223> OTHER INFORMATION: Oligonucleotide

<400> SEQUENCE: 24
gggtattgtg gcatgtttaa ccg                                          23

<210> SEQ ID NO 25
<211> LENGTH: 20
<212> TYPE: DNA
<213> ORGANISM: Artificial sequence
<220> FEATURE:
<223> OTHER INFORMATION: Oligonucleotide

<400> SEQUENCE: 25
gatggcagat gacagtacgc                                              20

<210> SEQ ID NO 26
<211> LENGTH: 16
<212> TYPE: DNA
<213> ORGANISM: Artificial sequence
<220> FEATURE:
<223> OTHER INFORMATION: Oligonucleotide

<400> SEQUENCE: 26
ccctctccct ttgtgg                                                  16
```

```
<210> SEQ ID NO 27
<211> LENGTH: 20
<212> TYPE: DNA
<213> ORGANISM: Artificial sequence
<220> FEATURE:
<223> OTHER INFORMATION: Oligonucleotide

<400> SEQUENCE: 27
cgacaattgg attcaccacg                                               20

<210> SEQ ID NO 28
<211> LENGTH: 21
<212> TYPE: DNA
<213> ORGANISM: Artificial sequence
<220> FEATURE:
<223> OTHER INFORMATION: Oligonucleotide

<400> SEQUENCE: 28
gcggtattga aaggttggtg c                                             21

<210> SEQ ID NO 29
<211> LENGTH: 20
<212> TYPE: DNA
<213> ORGANISM: Artificial sequence
<220> FEATURE:
<223> OTHER INFORMATION: Oligonucleotide

<400> SEQUENCE: 29
cgatactctg cgtctgcgtg                                               20

<210> SEQ ID NO 30
<211> LENGTH: 22
<212> TYPE: DNA
<213> ORGANISM: Artificial sequence
<220> FEATURE:
<223> OTHER INFORMATION: Oligonucleotide

<400> SEQUENCE: 30
gcaaaagcaa cagatagaac gg                                            22

<210> SEQ ID NO 31
<211> LENGTH: 21
<212> TYPE: DNA
<213> ORGANISM: Artificial sequence
<220> FEATURE:
<223> OTHER INFORMATION: Oligonucleotide

<400> SEQUENCE: 31
cgcttatctg acctctggtt c                                             21

<210> SEQ ID NO 32
<211> LENGTH: 19
<212> TYPE: DNA
<213> ORGANISM: Artificial sequence
<220> FEATURE:
<223> OTHER INFORMATION: Oligonucleotide

<400> SEQUENCE: 32
gcacgccttc actcaccag                                                19

<210> SEQ ID NO 33
<211> LENGTH: 21
<212> TYPE: DNA
<213> ORGANISM: Artificial sequence
<220> FEATURE:
<223> OTHER INFORMATION: Oligonucleotide
```

```
<400> SEQUENCE: 33
cggtttgcca ccatcctgtc g                                       21

<210> SEQ ID NO 34
<211> LENGTH: 20
<212> TYPE: DNA
<213> ORGANISM: Artificial sequence
<220> FEATURE:
<223> OTHER INFORMATION: Oligonucleotide

<400> SEQUENCE: 34
cgttaatcag gcaaagaggg                                         20
```

US 8,945,888 B2

METHOD FOR PRODUCING HIGH AMOUNT OF GLYCOLIC ACID BY FERMENTATION

CROSS REFERENCE TO RELATED APPLICATIONS

This application is a §371 National Stage Application of PCT/EP2010/053758, filed Mar. 23, 2010, which claims priority to European Application No. 09155971.6, filed Mar. 24, 2009, and U.S. Provisional Application No. 61/162,712, filed Mar. 24, 2009.

FIELD OF THE INVENTION

The present invention relates to an improved method for the bioconversion of a fermentable carbon source to glycolic acid by a recombinant microorganism bearing new genetic modifications such as ΔldhA, ΔmgsA, ΔarcA, and ΔlldP, ΔglcA, ΔyjcG and combination of them allowing a production with higher yield, titer and productivity.

BACKGROUND OF THE INVENTION

Glycolic acid ($HOCH_2COOH$) is the simplest member of the alpha-hydroxy acid family of carboxylic acids. Glycolic acid has dual functionality with both alcohol and moderately strong acid functional groups on a very small molecule. This results in unique chemical attributes as well as typical acid and alcohol chemistry.

Glycolic acid uses both the hydroxyl and carboxylic acid groups to form five-member ring complexes (chelates) with polyvalent metals. This metal ion complexing ability is useful in dissolution of hard water scale and prevention of deposition, especially in acid cleaning applications where good rinsibility is a key factor. Its properties make it ideal for a broad spectrum of consumer and industrial applications, including use in water well rehabilitation, the leather industry, the oil and gas industry, the laundry and textile industry, and as a component in personal care products. Glycolic acid undergoes reactions with organic alcohols and acids to form esters. Low molecular weight alkyl glycolic esters have unusual solvency properties and may be used as a substitute for n- and iso-propanol, ethylenediamine, phenol, m-cresol, 2-ethoxyethyl acetate, and ethyl and methyl lactate. Higher molecular weight alkyl esters can be used in personal care product formulations.

Glycolic acid can also be used to produce a variety of polymeric materials, including thermoplastic resins comprising polyglycolic acid. Resins comprising polyglycolic acid have excellent gas barrier properties, and such thermoplastic resins comprising polyglycolic acid may be used to make packaging materials having the same properties (e.g., beverage containers, etc.). The polyester polymers gradually hydrolyze in aqueous environments at controllable rates. This property makes them useful in biomedical applications such as dissolvable sutures and in applications where a controlled release of acid is needed to reduce pH. Currently more than 15,000 tons of glycolic acid are consumed annually in the United states.

The biological production of glycolic acid from an inexpensive carbon substrate such as glucose or other sugars, presented in FIG. 1, is disclosed in WO 2007/140816 and WO 2007/141316 respectively which content is incorporated herein by reference. The microorganism described in these applications is genetically engineered at different levels:
 to enhance the flux in the glyoxylate pathway,
 to increase the conversion of glyoxylate into glycolate and,
 to reduce the metabolism of glycolate and it intermediate, the glyoxylate.

The modifications have a direct impact on the terminal reactions of the glycolate synthesis pathway or on the closest intermediates of the glycolate. They all have the same objective, to direct the carbon flux at the production of glycolic acid and to prevent the catabolism of it.

The biological production of glycolic acid requires the formation of glyoxylate as an intermediate which is reduced to glycolate by a NADPH dependent oxidoreductase encoded by the gene ycdW (Nunez et al, (2001) Biochemistry, 354, 707-715). Glyoxylate is an intermediate of the glyoxylate cycle, a shunt of the TCA cycle (Tricarboxylic acid cycle and glyoxylate bypass, reviewed in Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. *Escherichia coli* and *Salmonella*: Cellular and Molecular Biology. American Society for Microbiology). Before getting into the TCA cycle, the carbon flux goes through glycolysis where several reactions take place and could be optimized to improve the production of the desired compound.

Glycolysis is a sequence of ten reactions involving ten intermediate compounds that converts glucose into pyruvate. The intermediates provide entry points to glycolysis and may also be directly or indirectly useful. For example, the intermediate dihydroxyacetone phosphate (DHAP) is a source of lactate via the protein MgsA. It is the same for the pyruvate molecule converted to lactate by the lactate dehydrogenase, LdhA. Both enzymes consume molecules of the glycolytic pathway meaning a part of the carbon flux to produce lactate, an undesired by-product in that case. The gene ldhA is attenuated in processes for production of succinate, such as in a rumen bacterial strain (WO2008/013405A1) or in *E.coli* for succinate production with a high yield. On the contrary, ldhA is overexpressed in processes aimed for the synthesis of lactate U.S. Pat. No. 7,700,332. The equivalent is found for mgsA, which is deleted among other genetic modifications for the production of the 1,3-propanediol (WO2004/033646A2), but overexpressed for the synthesis of the 1,2-propanediol (WO02008/116852A1). By attenuating both activities the production of glycolic acid should be improved and as the same time the synthesis of lactate should be reduced.

In the same manner every genetic modification that rises glycolytic and TCA fluxes, glucose import or catalytic activity of glycolytic and TCA enzymes would improve the production of glycolate. The attenuation of ArcA activity is one of such mutation. Indeed, the protein was shown as to be involved in repression of genes encoding the enzymes mentioned above.

The understanding of the global regulation by the Arc system started with the paper by Iuchi and Lin in 1988 (Iuchi and Lin, 1988, PNAS; 85: 1888-1892) describing the identification of the arcA gene and the effect of its mutation on the aerobic metabolism in *E. coli*. The two-component signal transduction system ArcAB (aerobic respiration control) modulates, at the transcriptional level, the expression of between 100 and 150 operons involved in energy metabolism, transport, survival, catabolism and in the redox state of the cell (Liu and DeWulf 2004, *J Biol Chem,* 279:12588-12597; Lynch and Lin, 1996 Responses to molecular oxygen; in Neidhardt F C, Curtiss III R J, Ingraham L, Lin ECC, Low K B, Magasanik B W, Zeznikoff S, Riley M, Schaechter M, Umbarger H E (eds) *Escherichia coli* and *Salmonella*: Cellular and Molecular Biology, ed 2. Washington, American Society for Microbiology, 1996, vol 1, pp 1526-1538). The main function of the ArcAB signal transduction pair is to regulate the transition from aerobic to anaerobic pathways in *E. coli*. Further understanding of the correlation between the aerobiosis level and the control exerted by global regulation was obtained from the work of Shalel-Levanon and colleagues (*Biotechnol. Bioeng.* 2005a; 89:556-564 and *Biotechnol. Bioeng.* 2005b; 92:147-159). These studies had shown the repression of the TCA genes by ArcA. These results were confirmed by complete physiological studies on the effect of ArcA on glucose catabolism in *E. coli* at different conditions of oxygen availability. Several changes have been observed in a ΔarcA mutant and under microaerobiosis; such as increased respiration, an altered electron flux distribution over the cytochrome o- and d-terminal oxidases, and a modification in the intracellular redox state (Aleexeva et al., 2003, *J. Bacteriol.* 185:204-209). The work of Perrenoud and Sauer in 2005 provided new insights onto ArcAB regulation, demonstrating that the control of aerobic and fully anaerobic TCA cycle fluxes was exerted by ArcA independently of its cognate sensor kinase, ArcB (*J. Bacteriol.* 2005, 187:3171-3179).

All those make ArcA a global regulator in *E. coli*. Its deletion is described in several patents claiming aerobiosis or anaerobiosis production of a desired molecule. For instance, ΔarcA improves the production of succinate and 1,2-propanediol in aerobiosis as in anaerobiosis (US 2006/0073577A1; WO2006/020663 and WO2008/116848). A decrease of ArcA activity among other genetic modifications was also disclosed in patents for the production of L-amino acid such as L-lysine and L-glutamic acid by Ajinomoto (EP 1 382686A1) and for the production of 1,3-propanediol (WO2004/033646) by DuPont de Nemours and Co.

Three proteins named GlcA, LldP and YjcG were characterized in the litterature as importers of glycolate and lactate (Nunez, F. et al., 2001 *Microbiology*, 147, 1069-1077; Nunez, F. et al., 2002 *Biochem. And Biophysical research communications* 290, 824-829; Gimenez, R. et al., 2003 *J. of Bacteriol.* 185, 21, 6448-6455). According to the publications mentioned above, GlcA seems to be more specific of glycolate and Lldp has more affinity for the lactate molecule. A strain wherein the three glycolate permeases are deleted is totally unable to import exogenous glycolate (Gimenez, R. et al., 2003 *J. of Bacteriol.* 185, 21, 6448-6455). The attenuation of the glycolate import of the strain producing glycolate would improve the ability of the cell to resist to high concentrations of glycolate and so, to improve the titer of production.

The problem to be solved by the present invention is the improvement of the biological production of glycolic acid from an inexpensive carbon substrate such as glucose or other sugars. Additional genetic modifications and in particular combination of them, are here described to get much better yield and titer of production of glycolic acid by fermentation.

SUMMARY OF THE INVENTION

The present invention provides an improved method for bioconverting with a high yield and titer a fermentable carbon source directly to glycolic acid.

In one aspect of this invention, a recombinant microorganism previously modified to produce glycolic acid further comprises several modifications, such as;
  attenuation of genes encoding lactate dehydrogenase (ldhA) and/or methylglyoxal synthase (mgsA),
  attenuation of the aerobic respiratory control regulator (arcA),
  attenuation of at least one of the genes glcA, lldP and yjcG, encoding the glycolate importer proteins.
According to the invention, the microorganism used in the method was previously genetically engineered to produce glycolic acid. Several modifications were previously introduced into said microorganism, and in particular modifications allowing the following metabolic changes:
  i) the microorganism cannot metabolize glyoxylate to other compounds than glycolate, by inactivating the genes coding for the malate synthases (aceB and glcB), the glyoxylate carboligase (gcl) and the 2-keto-3-deoxy-gluconate 6-phosphate aldolase (eda),
  ii) the microorganism cannot metabolize glycolate, by attenuating genes glcDEFG and aldA,
  iii) the glyoxylate pathway flux is increased by attenuation of icd, acek, pta, ackA, poxB, iclR or fadR and/or by overexpression of aceA,
  iv) the conversion of glyoxylate to glycolate is increased by using endogenous encoding genes like ycdW,
  v) the availability of NADPH is increased by attenuation of genes pgi, udhA and edd.

In another embodiment, the invention also provides a process for the production of glycolic acid from a recombinant microorganism comprising:
  (a) contacting the recombinant microorganism of the present invention with at least one carbon source selected from the group consisting of monosaccharides, oligosaccharides, polysaccharides, and single-carbon substrates whereby glycolate is produced; optionally
  (b) recovering the glycolic acid produced in through a step of polymerization to at least glycolic acid dimers and
  (c) recovery of glycolic acid by depolymerisation from glycolic acid dimers, oligomers and/or polymers.

BRIEF DESCRIPTION OF THE DRAWINGS

The accompanying drawings which are incorporated in and constitute a part of this specification exemplify the invention and together with the description, serve to explain the principles of this invention.

DETAILED DESCRIPTION OF THE INVENTION

Figure 1:
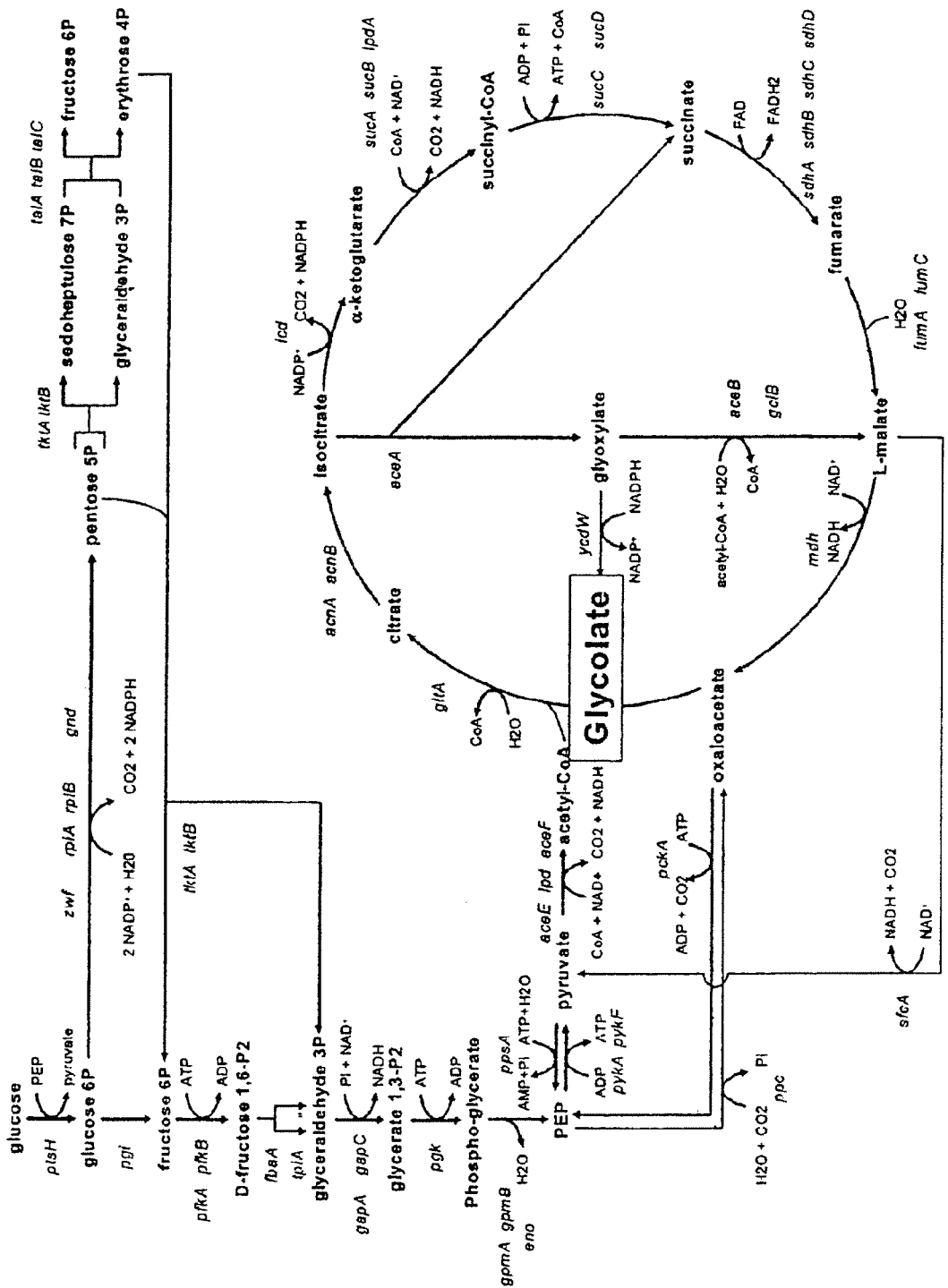
FIG. 1 depicts the genetic engineering of glycolysis, TCA cycle and glyoxylate pathway in the development of glycolic acid production system from carbohydrates.

Unless defined otherwise herein, all technical terms and scientific terms used herein have the same meaning as commonly understood by one of ordinary skill in the art to which this invention pertains.

In the present invention, the terms "microorganism" and "bacteria" are used interchangeably and refers to gram negative bacteria. In a preferred embodiment of the invention, microorganisms belong to the family of Enterobacteriaceae. The Enterobacteriaceae family comprises, in particular but not exclusively, the genera *Escherichia, Klebsiella, Salmonella* and *Pantoea*.

The term "mutant strain" refers to a non-wild type strain.

As used herein, the term "recombinant" or "genetically modified" or "modified microorganism" refer to a host cell that has a modification of its genome, e.g., as by addition of nucleic acid not naturally occurring in the organism or by a modification of nucleic acid naturally occurring in the host cell. The term "transformation" or "transfection" refers to the acquisition of new genes in a cell after the incorporation of exogenous nucleic acid. The term "transformant" refers to the product of a transformation.

The term "modification" or "modifying" the level of protein or enzyme activity produced by a host cell refers to controlling the levels of protein or enzymatic activity produced during culturing, such that the levels are increased or decreased as desired. The term "modified" when referring to nucleic acid or a polynucleotide means that the nucleic acid has been altered in some way as compared to a wild type nucleic acid, such as by mutation in; substitution, insertion, deletion of a part or all the nucleic acid; or by being operably linked to a transcriptional control region. Examples of mutations include but are not limited to point mutations, frame shift mutations, and deletions of part or all of mentioned genes.

By a "gene" is meant a segment of DNA involved in the encoding for regulatory RNA's, transfer RNA's, ribosomal RNA's promoter regions operably linked to the expression of a peptide, polypeptide or protein, including the coding region, non-coding region preceding ("leader") and following ("tailer") the coding region, as well as intervening non-coding sequences ("introns") between individual coding segments ("exons"). Coding refers to the representation of amino acids, start and stop signals in a three base "triplet" code.

The term "operably linked" refers to a juxtaposition wherein the elements are in an arrangement allowing them to be functionally related. A promoter is operably linked to a coding sequence if it controls the transcription of the sequence and a ribosome binding site is operably linked to a coding sequence if it is positioned so as to permit translation of the mRNA.

The term "inactivation" or "attenuation" refers to a decreased expression of a gene or a decreased activity of the protein, product of the gene. The man skilled in the art knows numerous means to obtain this result, and for example:

Introduction of a mutation into the gene, decreasing the expression level of this gene, or the level of activity of the encoded protein.
Replacement of the natural promoter of the gene by a low strength promoter, resulting in a lower expression.
Use of elements destabilizing the corresponding messenger RNA or the protein
Deletion of the gene if no expression is needed.

The term "expression" refers to the transcription and translation from a gene to the protein, product of the gene.

The term "overexpression" or "overexpressed" is defined herein to be at least 150% of protein activity as compared with an appropriate control species. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like.

The term "plasmid" or "vector" as used herein refers to an extra chromosomal element often carrying genes which are not part of the central metabolism of the cell, and usually in the form of circular double-stranded DNA molecules.

The term "carbon substrate", "carbon source" or "fermentable carbon source" means any carbon source capable of being metabolized by a microorganism wherein the substrate contains at least one carbon atom.

The term "ATCC" will stand for the American Type Culture Collection, 12301 Parklawn Drive, Rockville, Md. 20852, U.S.A.

The terms "glyoxylate" and "glyoxylic acid" are used interchangeably.

The terms "glycolate" and "glycolic acid" are used interchangeably. The term "glycolic acid, its derivatives or precursors" designates all intermediate compounds in the metabolic pathway of formation and degradation of glycolic acid. Precursors of glycolic acid are in particular:citrate, isocitrate, glyoxylate, and in general all compounds of the glyoxylate cycle (see FIG. 1). Derivatives of glycolic acid are in particular glycolate esters such as ethyl glycolate ester, methyl glycolate ester and polymers containing glycolate such as polyglycolic acid.

In the description of the present invention, enzymes are identified by their specific activities. This definition thus includes all polypeptides that have the defined specific activity also present in other organisms, more particularly in other microorganisms. Often enzymes with similar activities can be identified by their grouping to certain families defined as PFAM or COG.

PFAM (protein families database of alignments and hidden Markov models; http://www.sanger.ac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; http://www.ncbi.nlm.nih.gov/COG/) are obtained by comparing protein sequences from 43 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website http://www.ncbi.nlm.nih.gov/BLAST/ with the default parameters indicated on that website. The sequences obtained can then be exploited (e.g., aligned) using, for example, the programs CLUSTALW (http://www.ebi.ac.uk/clustalw/) or MULTALIN (http://prodes.toulouse.inra.fr/multalin/cgi-bin/multalin.pl), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (1989 Molecular Cloning: a Laboratory Manual. $2^{nd}$ ed. Cold Spring Harbor Lab., Cold Spring Harbor, New York.).

Genes identified in the present application with reference to *E. coli* can be found in all gram negative bacteria.

The present invention provides for an improved method for bioconverting a fermentable carbon source directly to glycolic acid using a single recombinant gram negative bacteria previously modified for producing glycolic acid and further genetically engineered to include at least one of the following modifications:

attenuation of the genes ldhA and mgsA
attenuation of the gene arcA
attenuation of at least one of the genes glcA, lldP and yjcG, to attenuate the membrane import of glycolate,
and combinations thereof.

All combinations of these modifications are possible and in particular:

attenuation of the genes ldhA and mgsA AND attenuation of the gene arcA;

attenuation of the genes ldhA and mgsA AND attenuation of the membrane import of glycolate;
attenuation of the gene arcA AND attenuation of the membrane import of glycolate;
attenuation of the genes ldhA and mgsA AND attenuation of the gene arcA AND attenuation of the membrane import of glycolate.

Genes are abbreviated as follows: lactate dehydrogenase (ldhA), methylglyoxal reductase (mgsA), aerobic respiratory control regulator A (arcA), L-lactate permease (lldP), glycolate permease (glcA) and acetate importer (yjcG).

The main advantage of these additional modifications is the improvement of the glycolic acid production by the engineered microorganism. Indeed, all these modifications lead to an improvement of the yield of production between 2% and 36% (from 0.39 g/g to 0.52 g/g compare to 0.38 g/g) as well as/or an improvement of the titer of glycolate between 9% and 28% (from 4.36 g/L to 5.14 g/L compare to 4.0 g/L).

A microorganism already modified to produce glycolic acid by fermentation is described in patent applications WO 2007/140816 and WO 2007/141316.

In one embodiment of the invention, the microorganism previously modified for producing glycolic acid comprises at least one of the following genetic modifications:

A low capacity of glyoxylate conversion, except to produce glycolate, due to the attenuation of genes encoding for enzymes consuming glyoxylate, a key precursor of glycolate: aceB and glcB genes encoding malate synthases, gcl encoding glyoxylate carboligase and eda encoding 2-keto-3-deoxygluconate 6-phosphate aldolase.

Modifications in such a way that the microorganism is unable to substantially metabolize glycolate. This result can be achieved by the attenuation of at least one of the genes encoding for enzymes consuming glycolate (glcDEFG encoding glycolate oxidase and aldA encoding glycoaldehyde dehydrogenase). Attenuation of genes can be done by replacing the natural promoter by a low strength promoter or by element destabilizing the corresponding messenger RNA or the protein. If needed, complete attenuation of the gene can also be achieved by a deletion of the corresponding DNA sequence.

An increase of the glyoxylate pathway flux by different means, and in particular:
i) Decreasing the activity of the enzyme isocitrate dehydrogenase (ICDH),
ii) Decreasing the activity of at least one of the following enzymes:
   phospho-transacetylase, encoded by the pta gene
   acetate kinase, encoded by the ackA gene
   pyruvate oxidase, encoded by the poxB gene by attenuation of the genes,
iii) Increasing the activity of the enzyme isocitrate lyase, encoded by the aceA gene,
iv) Decreasing the activity of the enzyme isocitrate dehydrogenase kinase/phosphatase AceK.

Decreasing the level of isocitrate dehydrogenase can be accomplished by introducing artificial promoters that drive the expression of the icd gene, coding for the isocitrate dehydrogenase, or by introducing mutations into the icd gene that reduce the enzymatic activity of the protein.

Since the activity of the protein ICDH is reduced by phosphorylation, it may also be controlled by introducing mutant aceK genes that have increased kinase activity or reduced phosphatase activity compared to the wild type AceK enzyme.

Increasing the activity of the isocitrate lyase can be accomplished either by attenuating the level of iclR or fadR genes, coding for glyoxylate pathway repressors, either by stimulating the expression of the aceA gene, for example by introducing artificial promoters that drive the expression of the gene, or by introducing mutations into the aceA gene that increase the activity of the encoded protein.

An increase activity catalyzing the conversion of glyoxylate into glycolate by expressing at least one gene encoding a polypeptide catalyzing the reaction. In particular, a gene encoding a NADPH dependent glyoxylate reductase enzyme is present to convert, under aerobic conditions, the toxic glyoxylate intermediate to the low toxicity final product glycolate. The gene can be exogenous or endogenous and can be expressed chromosomally or extra chromosomally. An NADPH-dependant glyoxylate reductase encoding gene can be taken among the ycdW or yiaE genes from the genome of E. coli MG1655. In a preferred embodiment, the expression of at least one of said genes is increased. If needed a high level of NADPH-dependant glyoxylate reductase activity can be obtained from chromosomally located genes by using one or several copies on the genome that can be introduced by methods of recombination known to the expert in the field. For extra chromosomal genes, different types of plasmids that differ with respect to their origin of replication and thus their copy number in the cell can be used. They may be present as 1-5 copies, ca 20 or up to 500 copies corresponding to low copy number plasmids with tight replication (pSC101, RK2), low copy number plasmids (pACYC, pRSF1010) or high copy number plasmids (pSK bluescript II). The ycdW or yiaE genes may be expressed using promoters with different strength that need or need not to be induced by inducer molecules. Examples are the promoters Ptrc, Ptac, Plac, the lambda promoter cI or other promoters known to the expert in the field. Expression of the genes may also be boosted by elements stabilizing the corresponding messenger RNA (Carrier and Keasling (1998) *Biotechnol. Prog.* 15, 58-64) or the protein (e.g. GST tags, Amersham Biosciences).

Increase NADPH availability to the NADPH-dependant glyoxylate reductase. This modification of the microorganism characteristics can be obtained through the attenuation of at least one of the genes selected among the following: pgi encoding the glucose-6-phosphate isomerase, udhA encoding the soluble transhydrogenase and edd encoding the 6-phosphogluconate dehydratase activity. With such genetic modifications, all the glucose-6-phosphate will have to enter glycolysis through the pentose phosphate pathway and 2 NADPH will be produced per glucose-6-phosphate metabolized.

In another embodiment of the invention, the microorganism previously modified for producing glycolic acid comprises in particular an attenuation of the gene aceK. The glyoxylate bypass enzyme ICL is in direct competition with the Krebs cycle enzyme isocitrate dehydrogenase (ICDH) for their common substrate and although ICDH has a much higher affinity for isocitrate, flux of carbon through ICL is assured by virtue of high intracellular level of isocitrate and the reversible phosphorylation/inactivation of a large fraction of ICDH. Reversible inactivation is due to reversible phosphorylation catalysed by ICDH kinase/phosphatase, named AceK, which harbours both catalytic activities on the same polypeptide (Laporte D C 1989, *Biochimie* September-October; 71(9-10):1051-7; Ikeda T P, 1992, *J Bacteriol*. February; 174(4):1414-6.; Cozzone A J, El-Mansi M. 2005, *J Mol Microbiol Biotechnol*. 9(3-4):132-46).

It would be advantageous for the process of the invention to fully control the activity of ICDH, by removing from the cell all known regulations including aceK. An aceK deletion may lead to an increased activity of ICDH. Nevertheless, lower artificial expression of the icd gene by genetic modification of its promoter will allow the construction of producer strains with a defined, low level of ICDH, permitting the production of glyoxylate and thus glycolate in an ΔaceK background.

In a specific embodiment of the invention, the microorganism initially modified for producing glycolic acid further comprises an attenuation of the genes ldhA and mgsA. The gene ldhA encodes the lactate dehydrogenase (EC 1.1.1.27) that converts pyruvate, the final product of glycolysis to lactic acid. The gene mgsA encodes the methylglyoxal synthase (EC 4.2.3.3) that converts dihydroxyacetone phosphate (DHAP) to methylglyoxal.

Both enzymes consume molecules which have a major biochemical role is in the glycolysis metabolic pathway and lead to the production of lactate. In order to save some carbon for the production of glycolate and to avoid the accumulation of lactate as a by-product, the deletion of ldhA and mgsA was done in the strain used in the method of the invention. The aim of such deletions is to improve the yield of glycolate production and to facilitate the purification of our product.

A further embodiment of the invention provides the method wherein the microorganism initially modified for producing glycolic acid additionally comprises an attenuation of the gene arcA. As used herein, "ArcA" and "arcA" refer to a polypeptide and coding region, respectively.

ArcA is one polypeptide of the two-component regulatory ArcAB system. Two-component signal transduction systems enable bacteria to sense, respond, and adapt to a wide range of environments, stresses, and growth conditions. In the prototypical two-component system, a sensor histidine kinase, catalyzes its autophosphorylation and then subsequently transfers the phosphoryl group to a response regulator, which can then effect changes in cellular physiology, often by regulating gene expression. For instance, ArcB is the membrane bound histidine kinase and ArcA the response regulator (Georgellis et al., 1999). The regulatory system allows $E.\ coli$ to respond to a wide range of oxygen concentrations—from fully aerobic to micro aerobic to fully anaerobic conditions.

ArcA controls expression of many operons in $E.\ coli$ and other gram negative bacteria. Included in the ArcA regulon are mainly the factors involved in pathways generating cellular energy from sugar substrates: several dehydrogenases of the flavoprotein class, terminal oxidases, tricarboxylic acid cycle enzymes, enzymes of the glyoxylate shunt, enzymes involved in the fermentative metabolism (Iuchi, S., and Lin, E. C. C. (1993) Mol. Microbiol. 9, 9-15; Bauer, C. E., Elsen, S., and Bird, T. H. (1999) Annu. Rev. Microbiol. 53, 495-523). ArcA causes decreased expression of many of those operons during anaerobic growth and during aerobic conditions at high growth rate (e.g., exponential growth) (S. Iuchi et al., Cell, 66, 5-7 (1991)). It is known that ArcA protein negatively controls expression of the genes for tricarboxylic acid cycle (TCA) enzymes. In an arcA-disrupted strain, the expression of the genes for the TCA cycle is increased (http://www-.genome.ad.jp/dbget-bin/get_htext?Exp_DB+-n+Bget-bin/get_htext?Exp_DB+-n+B).

In order to improve the productivity and the yield of glycolate synthesis, the gene arcA is deleted in the strain used in the method of the invention. Indeed, ΔarcA combined with the genetic modifications, previously done in the strain should raise the flux in the TCA cycle and in the glyoxylate shunt toward the production of glycolate.

Moreover, ArcA was demonstrated as to be involved in the regulation of PTS expression in response to the cellular redox status (Jeong, J-Y. et al., 2004, Journal of Bio. Chem.). The phosphorylated form of ArcA represses ptsG transcription from the P1 promoter. Even if ArcA is phosphorylated mainly in anaerobic conditions; ArcB being auto-phosphorylated in absence of oxygen, we cannot not exclude that ArcA would be phosphorylated by a kinase of another two-component system (cross-reaction) in aerobic conditions (Laub, M. T. and Goulian, M. Annu. Rev. Genet. (2007); 41:121-45). Therefore, we cannot exclude a repression of ptsG expression by ArcA-P in aerobic conditions This is another reason of the deletion of arcA gene in glycolate producing strains used in the process described in the present invention.

In another embodiment of the invention, the microorganism initially modified for producing glycolic acid further comprises attenuation of the glycolate membrane import. In particular at least one of the genes glcA, lldP and yjcG encoding glycolate impoters is attenuated.

Membrane import protein (or simply importer) is a protein involved in the movement of ions, small molecules, or macromolecules, such as another protein across a biological membrane. Import proteins are integral membrane proteins; that is they exist within and span the membrane across which they import substances. The proteins may assist in the movement of substances by facilitated diffusion or active import. The three proteins mentioned above were all characterized as importers of glycolate and lactate (Nunez, F. et al., 2001 Microbiology, 147, 1069-1077; Nunez, F. et al., 2002 Biochem. And Biophysical research communications 290, 824-829; Gimenez, R. et al., 2003 J. of Bacteriol. 185, 21, 6448-6455). A strain mutated on each glycolate permease cannot grow on glycolate as carbon source demonstrating that the strain is unable to import glycolate (Gimenez, R. et al., 2003). By attenuating the glycolate import into the cell used to produce glycolic acid the aim is to improve the capability of the strain to resist and accumulate glycolic acid and so to improve the titer of production.

In a specific embodiment of the invention, the three genes glcA, lldP, and yjcG are attenuated.

It would be also advantageous to increase the exportation of glycolic acid from this glycolic acid producing microorganism. The man skilled in the art knows numerous means to obtain such increase in the export of a specific metabolite, in particular enhancing the activity and/or the expression of an export protein, able to export glycolic acid from the microorganism to the medium.

A specific embodiment the invention provides a method for the fermentative production of glycolic acid from a recombinant organism comprising:

(a) contacting the recombinant organism of the present invention with at least one carbon source selected from the group consisting of glucose, sucrose, monosaccharides (such as fructose, mannose, xylose, arabinose), oligosaccharides (such as galactose, cellobiose, . . . ), polysaccharides (such as cellulose), starch or its derivatives, glycerol and single-carbon substrates whereby glyoxylic acid is produced, (b) Optionally, the process comprises a step of concentration of glycolate in the bacteria or in the medium and isolation of glycolic acid from the fermentation broth and/or the biomass optionally remaining in portions or in the total amount (0-100%) in the end product, Optionally the process comprises a step of recovery of the glycolic acid produced in step (a) through a step of polymerization to at least glycolic acid dimers and (c) isolation and recovery of glycolic acid from the fermentation broth and/or the biomass, optionally remaining in portions or in the total amount in the end product, by depolymerisation from glycolic acid dimers, oligomers and/or polymers.

Those skilled in the art are able to define the culture conditions for the microorganisms according to the invention. In particular the gram negative bacteria are fermented at a temperature between 20° C. and 55° C., preferentially between 25° C. and 40° C., and more specifically about 37° C. for *E. coli*.

The fermentation is generally conducted in fermenters with an inorganic culture medium of known defined composition adapted to the bacteria used, containing at least one simple carbon source, and if necessary a co-substrate necessary for the production of the metabolite.

The invention is also related to the microorganism as described previously. Preferably, said microorganism belongs to the family of Enterobacteriaceae. More preferentially, the microorganism is from the genus *Escherichia*, and even more preferentially is *Escherichia coli*.

EXAMPLES

Several protocols were used to build the strains producing glycolic acid described in the following examples. The protocols are detailed below.

Protocol 1: Introduction of a PCR Product for Recombination and Selection of the Recombinants (FRT System)

The oligonucleotides chosen and given in Table 1 for replacement of a gene or an intergenic region were used to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ Red (γ, β, exo) expressed greatly favours homologous recombination. The antibiotic-resistant transformants were then selected and the insertion of the resistance cassette was checked by PCR analysis with the appropriate oligonucleotides given in Table 2.

Protocol 2: Elimination of Resistance Cassette (FRT System)

The chloramphenicol and/or kanamycin resistance cassettes were eliminated according to the following technique. The plasmid pCP20 carrying the FLP recombinase acting at the FRT sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 2.

Protocol 3: Transduction with Phage P1 for Deletion of a Gene

The deletion of the chosen gene by replacement of the gene by a resistance cassette (kanamycin or chloramphenicol) in the recipient *E. coli* strain was performed by the technique of transduction with phage P1. The protocol was in two steps, (i) the preparation of the phage lysate on the donor strain with a single gene deleted and (ii) the transduction of the recipient strain by this phage lysate.

Preparation of the Phage Lysate

Seeding with 100 µl of an overnight culture of the strain MG1655 with a single gene deleted of 10 ml of LB+Cm 30 µg/ml+glucose 0.2%+CaCl$_2$ 5 mM.

Incubation for 30 min at 37° C. with shaking.

Addition of 100 µl of phage lysate P1 prepared on the donor strain MG1655 (approx. 1×10$^9$ phage/ml).

Shaking at 37° C. for 3 hours until all cells were lysed.

Addition of 200 µl of chloroform, and vortexing.

Centrifugation for 10 min at 4500 g to eliminate cell debris.

Transfer of supernatant in a sterile tube and addition of 200 µl of chloroform.

Storage of the lysate at 4° C.

Transduction

Centrifugation for 10 min at 1500 g of 5 ml of an overnight culture of the *E. coli* recipient strain in LB medium.

Suspension of the cell pellet in 2.5 ml of MgSO$_4$ 10 mM, CaCl$_2$ 5 mM.

Control tubes: 100 µl cells

100 µl phages P1 of the strain MG1655 with a single gene deleted.

Tube test: 100 µl of cells+100 µA phages P1 of strain MG1655 with a single gene deleted.

Incubation for 30 min at 30° C. without shaking.

Addition of 100 µl sodium citrate 1 M in each tube, and vortexing.

Addition of 1 ml of LB.

Incubation for 1 hour at 37° C. with shaking.

Plating on dishes LB+Cm 30 µg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 2.

Protocol 4: Introduction of a PCR Product for Recombination and Selection of the Recombinants (Cre-LOX System)

The oligonucleotides chosen and given in Table 1 for replacement of a gene or an intergenic region were used to amplify either the chloramphenicol resistance cassette from the plasmid loxP-cm-loxP (Gene Bridges) or the neomycin resistance cassette from the plasmid loxP-PGK-gb2-neo-loxP (Gene Bridges). The PCR product obtained was then introduced by electroporation into the recipient strain bearing the plasmid pKD46 in which the system λ Red (γ, β, exo) expressed greatly favours homologous recombination. The antibiotic-resistant transformants were then selected and the insertion of the resistance cassette was checked by PCR analysis with the appropriate oligonucleotides given in Table 2.

Protocol 5: Elimination of Resistance Cassettes (Cre-LOX System)

The chloramphenicol and/or kanamycin resistance cassettes were eliminated according to the following technique. The plasmid pJW168 (Palmeros B. et al (2000), *Gene* 247: 255-264) carrying the Cre recombinase acting at the Cre-LOX sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 2.

TABLE 1

Oligonucleotides used for the constructions described in the following examples

| Gene | Names of oligos | SEQ ID N° | Homology with chromosomal region (Ecogene) | Sequences |
|---|---|---|---|---|
| icd | Ome 703 Ptrc-icd F | N° 1 | 1194281-1194345 | GGACGCAAACGCATATGCAACGTGGTGGCAGACG AGCAAACCAGTAGCGCTCGAAGGAGAGGTGATCA CACTGGCTCACCTTCGGGTGGGCCTTTCTGCCATAT GAATATCCTCCTTAG |

TABLE 1-continued

Oligonucleotides used for the constructions described in the following examples

| Gene | Names of oligos | SEQ ID N° | Homology with chromosomal region (Ecogene) | Sequences |
|---|---|---|---|---|
| | Oag 30<br>Ptrc icd R2 | N° 2 | 1194402-1194347 | GCCGTTTTGCAGGGTGATCTTCTTGCCTTGTGCCGG<br>AACAACTACTTTACTTTCCAAAGCTGTTTCCTTCTT<br>ACCACACAGTATACGAGCCGGATGATTAATCGCCA<br>ACAGCTCTGTAGGCTGGAGCTGCTTCG |
| ldhA | ldhAF (Opg 0013)<br>DldhA F | N° 3 | 1440865-1410786 | GAAACTCGCCGTTTATAGCACAAAACAGTACGACA<br>AGAAGTACCTGCAACAGGTGAACGAGTCCTTTGGC<br>TTTGAGCTGGTGTAGGCTGGAGCTGCTTCG |
| | ldhAR (Opg 0014)<br>DldhA R | N° 4 | 1439878-1439958 | TTAAACCAGTTCGTTCGGGCAGGTTTCGCCTTTTTC<br>CAGATTGCTTAAGTTTTGCAGCGTAGTCTGAGAAA<br>TACTGGTCAGCATATGAATATCCTCCTTAG |
| mgsA Km | DmgsAKF | N° 5 | 1026316-1026245 | GCAGGCTTTTTCGGTCTTTATCTTGCAGCGATAAGT<br>GCTTACAGTAATCTGTAGGAAAGTTAACTACGGAT<br>GATTCCGGGGATCCGTCGACCTGCAGTTC |
| | DmgsAKR | N° 6 | 1025721-1025800 | GGATGTGCCGGTGGCGAGAAAACCGTAAGAAACA<br>GGTGGCGTTTGCCACCTGTGCAATATTACTTCAGAC<br>GGTCCGCGAGTGTAGGCTGGAGCTGCTTCG |
| mgsA Cm | Obu 0085<br>DmgsA F | N° 7 | 1026273-1026193 | GTAATCTGTAGGAAAGTTAACTACGGATGTACATT<br>ATGGAACTGACGACTCGCACTTTACCTGCGCGGAA<br>ACATATTGCGCCATATGAATATCCTCCTTAG |
| | Obu 0086<br>DmgsA R | N° 8 | 1025758-1025838 | GGCGTTTGCCACCTGTGCAATATTACTTCAGACGGT<br>CCGCGAGATAACGCTGATAATCGGGGATCAGAATA<br>TCGACCGCGTGTAGGCTGGAGCTGCTTCG |
| arcA | Ome 914<br>DarcAF | N° 9 | 4638322-4638245 | CCCCGCACATTCTTATCGTTGAAGACGAGTTGGTA<br>ACACGCAACACGTTGAAAAGTATTTTCGAAGCGGA<br>AGGCTATGTGTAGGCTGGAGCTGCTTCG |
| | ome 915<br>DarcAR | N° 10 | 4637621-4637699 | CCAGATCACCGCGAAAGCGATAACCTTCACCGTGA<br>ATGGTGGCGATGATTTCCGGCGTATCCGGCGTAGA<br>TTCGAAATGCATATGAATATCCTCCTTAG |
| glcA | DglcA-loxP F<br>Oag 0123<br>DglcA-loxP F | N° 11 | 3119299-3119221 | GGTTACCTGGACCCAAATGTATATGCCGATGGGAG<br>GACTGGGGCTATCCGCTCTGGTCGCCCTGATCCCG<br>ATAATATTCAATTAACCCTCACTAAAGGG |
| | DglcA-loxP R<br>Oag 0124<br>DgIcA-loxP R | N° 12 | 3117622-3117701 | CGAGACTAACATCCCGGTAAACATACGCCTGCA<br>GCAGGGTGATAATGCCGATAACGCTGGCAAAAATC<br>AGACTGTGCTAATACGACTCACTATAGGG |
| lldP | DlldP F<br>Oag 0051<br>DlldP F | N° 13 | 3775414-3775493 | GACCTGCAATGAATCTCTGGCAACAAAACTACGAT<br>CCCGCCGGGAATATCTGGCTTTCCAGTCTGATAGC<br>ATCGCTTCCCCATATGAATATCCTCCTTAG |
| | DlldP R<br>Oag 0052<br>DlldP R | N° 14 | 3777054-3776976 | CATAAGCCTGAAGCGTGGTGATCACGCCCACTATA<br>CAGGTGAAGATCAGGCTGTGTTTGACAGTAAAGCG<br>GAACAAATCTGTAGGCTGGAGCTGCTTCG |
| yjcG | DyjcGF<br>Oag 0133<br>DyjcGF | N° 15 | 4282916-4282835 | GTTCTGACGGCGCTTGCCGCCACACTCCCTTTCGCA<br>GCTAACGCCGCGGATGCTATTAGCGGGGCCGTAGA<br>GCGCCAGCCAATTAACCCTCACTAAAGGG |
| | DyjcGR<br>Oag 0134<br>DyjcGR | N° 16 | 4281281-4281360 | GCGCGCGGCCTTGCTCAACGCCAAAGCCGGTCTGG<br>GAGCGGATAAACTGCGCGCGGAACAGTTCACGCTC<br>ACGCGCGCCTAATACGACTCACTATAGGG |
| pME101-ycdW-TT7- | Oag 0033 | N° 17 | 1097384-1097416 | CCTACCGGTATGGGCGAGCAAATGCAGGAATATGC<br>Part of ycdW |
| PaceA-aceA-TT01 | Oag 0034 | N° 18 | 1098047-1098016 | GCATGCATCCCGGGGCAGAAAGGCCCACCCGAAG<br>GTGAGCCAGTGTGAAGATCTTTAGTAGCCGCGTGC<br>GCGGTCGACTTGCCCGC<br>End of ycdW + the terminator TT7 |

TABLE 1-continued

Oligonucleotides used for the constructions described in the following examples

| Gene | Names of oligos | SEQ ID N° | Homology with chromosomal region (Ecogene) | Sequences |
|---|---|---|---|---|
| | Oag 0037 | N° 19 | 4213337-4213361 | CCCAAGCTTCATATTGTTATCAACAAGTTATC Promoteur aceBAK and beginning of aceA |
| | Oag 0038 | N° 20 | 4216438-4216419 | TCCCCCGGGGCTTAGAACTGCGATTCTTC End of aceA |

TABLE 2

Oligonucleotides used for checking the insertion of a resistance cassette or the loss of a resistance cassette

| Gene | Names of oligos | SEQ ID N° | Homology with chromosomal region | Sequences |
|---|---|---|---|---|
| icd | Ome 704 seq Ptrc-icd F | N° 21 | 1194153-1194173 | CAGAGATTATGAATTGCCGCA |
| | Ome 705 seq Ptrc-icd R | N° 22 | 1194540-1194520 | CCAGGAGATTTTACGCTCGCC |
| IdhA | Opg 0011 ldhAF | N° 23 | 1439724-1439743 | GCCATCAGCAGGCTTAGCGC |
| | Opg 0012 ldhAR | N° 24 | 1441029-1441007 | GGGTATTGTGGCATGITTAACCG |
| mgsA Km et Cm | Opg 0122 yecT R | N° 25 | 1026499-1026480 | GATGGCAGATGACAGTACGC |
| | Opg 0123 helD F2 | N° 26 | 1025689-1025704 | CCCTCTCCCTTTGTGG |
| arcA | Ome 0916 arcAF | N° 27 | 4638746-4638727 | CGACAATTGGATTCACCACG |
| | Ome 0917 arcAR | N° 28 | 4637308-4637328 | GCGGTATTGAAAGGTTGGTGC |
| glcA | Oag 0049 glcA F | N° 29 | 3119492-3119473 | CGATACTCTGCGTCTGCGTG |
| | Oag 0050 glcA R | N° 30 | 3117387-3117408 | GCAAAAGCAACAGATAGAACGG |
| lldP | Oag 0053 lldP F | N° 31 | 3775227-3775247 | CGCTTATCTGACCTCTGGTTC |
| | Oag 0054 lldR R | N° 32 | 3777257-3777239 | GCACGCCTTCACTCACCAG |
| yjcG | Opg 0076 yjcHF | N° 33 | 4283167-4283147 | CGGTTTGCCACCATCCTGTCG |
| | Opg 0077 yjcFR | N° 34 | 4281047-4281066 | CGTTAATCAGGCAAAGAGGG |

Example 1

Figure 2:
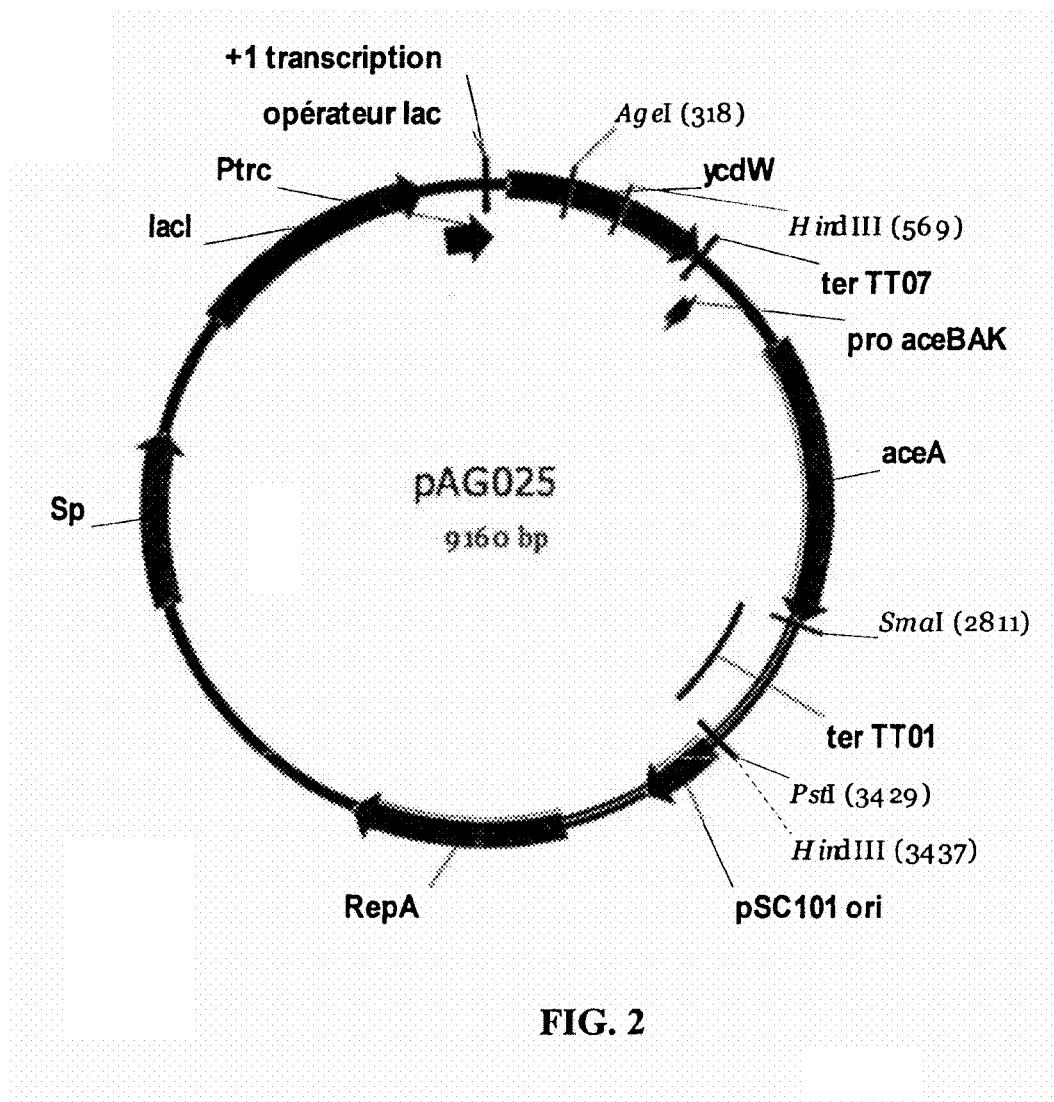
FIG. 2 is a diagram showing the construction of the vector pME101-ycdW-TT07-PaceA-aceA-TT01, named pAG25.
Figure 3:
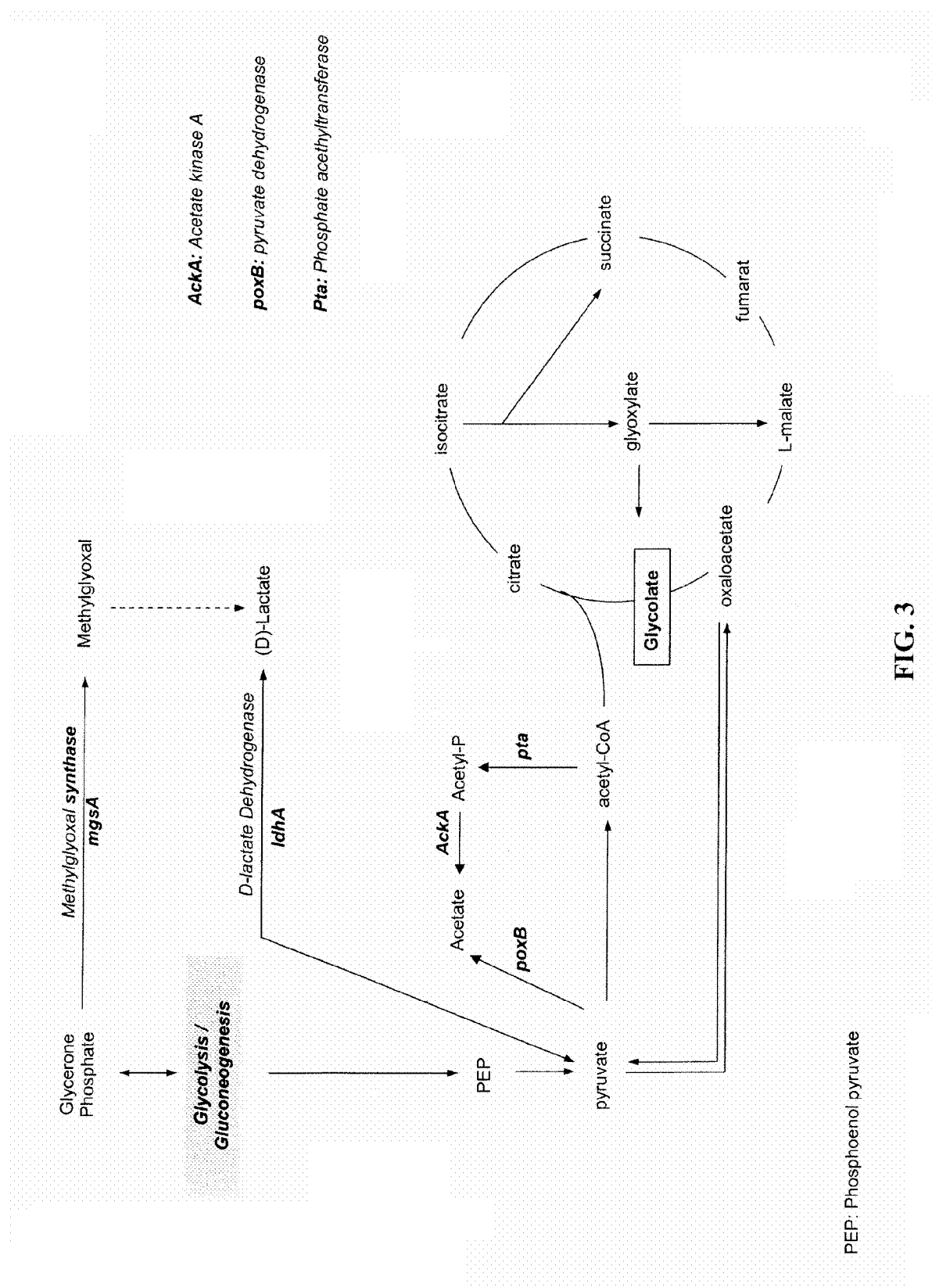
FIG. 3 is a zoom in on lactate and acetate pathways. Some of the genes involved in theses pathways are modified in the invention.

Construction of the plasmid pME101-ycdW-TT07-PaceA-aceA-TT01 (FIG. 2)

The plasmid pME101-ycdW-TT07-PaceA-aceA-T101 was built in three steps from the plasmid pME101-ycdW whose description is given in patent applications PCT/EP2006/063046 and PCT/EP2007/055625 and from the plasmid pJB137-aceA.

The first step was to build the plasmid pME101-ycdW-TT07 by adding a terminator to the end of ycdW. The end of the gene ycdW is amplified by PCR done on genomic DNA with the oligonucleotides including the TT07 in their sequence and shown in table 1. The PCR fragment digested with AgeI/SmaI was cloned into the plasmid pME101-ycdW cut by the same restriction enzymes to lead to the plasmid pME101-ycdW-TT7.

The plasmid pJB137-aceA was built by cloning a PCR fragment in the plasmid pJB137 (EMBL Accession number U75326) digested with SmaI/HindIII. The PCR fragment was realized on genomic DNA purified from an MG1655 ΔaceB strain described in patent applications PCT/EP2006/063046 and PCT/EP2007/055625 and oligonucleotides (Oag0037 and Oag0038) described in the table 1. The gene aceA as its own promoter were amplified before to be cloned into the plasmid.

The last step was to cut the plasmid pJB137-aceA to get the fragment PaceA-aceA-TT01, TT01 being the terminator of the pJB137. The plasmid pJB137-aceA was cut with HindIII, treated with the Klenow enzyme and lastly digested by PstI restriction enzyme. The resulting DNA fragment was then cloned into the plasmid pME101-ycdW-TT07 opened sequentially with SmaI and PstI. The resulting plasmid was pME101-ycdW-TT07-PaceA-aceA-TT01, named pAG025.

Example 2

Construction of a Strain Able to Produce Glycolic Acid by Fermentation: MG1655 Ptrc50/RBSB/TTG-icd::Cm ΔaceB Δgcl ΔglcDEFGB ΔaldA ΔiclR Δedd+eda ΔpoxB ΔackA+pta (pME101-ycdW-TT07-PaceA-aceA-TT01)

The strain E. coli MG1655 ΔaceB Δgcl ΔglcDEFGB ΔaldA ΔiclR Δedd+eda ΔpoxB ΔackA+pta was built according to the description given in patent applications PCT/EP2006/063046 and PCT/EP2007/055625.

The attenuation of icd transcription was realized by substitution of the natural icd promoter by an artificial one called Ptrc50/RBSB/TTG carrying a chloramphenicol resistance cassette, in the strain E. coli MG1655 ΔaceB Δgcl ΔglcDEFGB ΔaldA ΔiclR Δedd+eda ΔpoxB ΔackA+pta. The construction is performed according to the technique described in the Protocol 1 with the respective oligonucleotides (Seq. No. 1 and No. 2) given in table 1. The chloramphenicol cassette is not eliminated.

The PCR fragment Ptrc50/RBSB/TTG-icd::Cm was first introduced by electroporation into the strain MG1655 (pKD46) to give the strain MG1655 Ptrc50/RBSB/TTG-icd::Cm, validated by sequencing.

In a second step, the attenuation icd construction was introduced into the strain MG1655 ΔaceB Δgcl ΔglcDEFGB ΔaldA ΔiclR Δedd+eda ΔpoxB ΔackA+pta by transduction (see protocol 3), to give the strain MG1655 Ptrc50/RBSB/TTG-icd::Cm ΔaceB Δgcl ΔglcDEFGB ΔaldA ΔiclR Δedd+eda ΔpoxB ΔackA+pta.

The plasmid pME101-ycdW-TT07-PaceA-aceA-TT01 (Example 1) was then introduced into the strain giving rise to MG1655 Ptrc50/RBSB/TTG-icd::Cm ΔaceB Δgcl ΔglcDEFGB ΔaldA ΔiclR Δedd+eda ΔpoxB ΔackA+pta (pME101-ycdW-TT07-PaceA-aceA-TT01), named AG0662.

Example 3

Construction of a Strain to Improve the Production of Glycolic Acid by Fermentation: MG1655 Ptrc50/RBSB/TTG-icd::Cm ΔaceB Δgcl ΔglcDEFGB ΔaldA ΔiclR Δedd+eda ΔpoxB ΔackA+pta ΔldhA (pME101-ycdW-TT07-PaceA-aceA-TT01)

The gene ldhA was inactivated in the strain E. coli MG1655 Ptrc50/RBSB/TTG-icd::Cm ΔaceB Δgcl ΔglcDEFGB ΔaldA ΔiclR Δedd+eda ΔpoxB ΔackA+pta (pKD46) by recombinaison with a PCR product done with the oligos No 3 and No 4 shown in table 1 (See Protocol 1). The resulting strain was MG1655 Ptrc50/RBSB/TTG-icd::Cm ΔaceB Δgcl ΔglcDEFGB ΔaldA ΔiclR Δedd+eda ΔpoxB ΔackA+pta ΔldhA::Km in which the plasmid pME101-ycdW-TT07-PaceA-aceA-TT01 (Example 1) was introduced in a last step. The final strain was called AG0708.

Example 4

Construction of a Strain to Improve the Production of Glycolic Acid by Fermentation: MG1655 Ptrc50/RBSB/TTG-icd::Cm ΔaceB Δgcl ΔglcDEFGB ΔaldA AMR Δedd+eda ΔpoxB ΔackA+pta ΔmgsA (pME101-ycdW-TT07-PaceA-aceA-TT01)

The gene mgsA was inactivated in the strain E. coli MG1655 Ptrc50/RBSB/TTG-icd::Cm ΔaceB Δgcl ΔglcDEFGB ΔaldA ΔiclR Δedd+eda ΔpoxB ΔackA+pta by the technique of transduction with phage P1 described in protocol 3. The donor strain MG1655 ΔmgsA::Km was built by introduction of a PCR fragment into the strain MG1655 (pKD46). The oligonucleotides used for the construction are presented in table 1. The strain was validated by sequencing.

The plasmid pAG025 was then introduced into the strain E. coli MG1655 Ptrc50/RBSB/TTG-icd::Cm ΔaceB Δgcl ΔglcDEFGB ΔaldA ΔiclR Δedd+eda ΔpoxB ΔackA+pta ΔmgsA::Km to lead to the final one named AG0819:MG1655 Ptrc50/RBSB/TTG-icd::Cm ΔaceB Δgcl ΔglcDEFGB ΔaldA ΔiclR Δedd+eda ΔpoxB ΔackA+pta ΔmgsA::Km (pME101-ycdW-TT07-PaceA-aceA-TT01).

Example 5

Construction of a Strain to Improve the Production of Glycolic Acid by Fermentation: MG1655 Ptrc50/RBSB/TTG-icd::Cm ΔaceB Δgcl ΔglcDEFGB ΔaldA ΔiclR Δedd+eda ΔpoxB ΔackA+pta ΔarcA (pME101-ycdW-TT07-PaceA-aceA-TT01)

The gene arcA was inactivated in the strain E. coli MG1655 Ptrc50/RBSB/TTG-icd::Cm ΔaceB Δgcl ΔglcDEFGB ΔaldA ΔiclR Δedd+eda ΔpoxB ΔackA+pta by the technique of transduction with phage P1 described in protocol 3. The donor strain MG1655 ΔarcA::Km was built by introduction of a PCR fragment into the strain MG1655 (pKD46). The oligonucleotides used for the construction are presented in table 1. The strain was validated by sequencing.

The plasmid pAG025 was then introduced into the strain E. coli MG1655 Ptrc50/RBSB/TTG-icd::Cm ΔaceB Δgcl ΔglcDEFGB ΔaldA ΔiclR Δedd+eda ΔpoxB ΔackA+pta ΔarcA::Km to lead to the final one named AG0956: MG1655 Ptrc50/RBSB/TTG-icd::Cm ΔaceB Δgcl ΔglcDEFGB ΔaldA ΔiclR Δedd+eda ΔpoxB ΔackA+pta ΔarcA::Km (pME101-ycdW-TT07-PaceA-aceA-TT01).

Example 6

Construction of a Strain to Improve the Production of Glycolic Acid by Fermentation: MG1655 Ptrc50/RBSB/TTG-icd::Cm ΔaceB Δgcl ΔglcDEFGB ΔaldA ΔiclR Δedd+eda ΔpoxB ΔackA+pta ΔldhA ΔmgsA (pME101-ycdW-TT07-PaceA-aceA-TT01)

In a first step the deletion ΔmgsA::Cm was done by phage transduction (protocol 3) into the strain MG1655 ΔaceB Δgcl ΔglcDEFGB ΔaldA ΔiclR Δedd+eda ΔpoxB ΔackA+pta to give the strain MG1655 ΔaceB Δgcl ΔglcDEFGB ΔaldA ΔiclR Δedd+eda ΔpoxB ΔackA+pta ΔmgsA::Cm. The donor strain MG1655 ΔmgsA::Cm was built by introduction of a PCR fragment into the strain MG1655 (pKD46). The oligonucleotides used for the construction are presented in table 1. The strain was validated by sequencing.

In a second step, the deletion ΔldhA::Km was done into the strain MG1655 ΔaceB Δgcl ΔglcDEFGB ΔaldA ΔiclR Δedd+eda ΔpoxB ΔackA+pta ΔmgsA::Cm by transduction from the donor strain MG1655 ΔldhA::Km (described in Example 3) to give the strain MG1655 ΔaceB Δgcl ΔglcDEFGB ΔaldA ΔiclR Δedd+eda ΔpoxB ΔackA+pta ΔmgsA::Cm ΔldhA::Km. The chloramphenicol and kanamycin resistance cassettes were eliminated according to the technique described in Protocol 2. The strain MG1655 ΔaceB Δgcl ΔglcDEFGB ΔaldA ΔiclR Δedd+eda ΔpoxB ΔackA+pta ΔmgsA ΔldhA was validated by PCR with the oligos shown in table 2.

In a third step, the construction Ptrc50/RBSB/TTG-icd::Cm was introduced by transduction from the strain MG1655 Ptrc50/RBSB/TTG-icd::Cm described in Example 2. The resulting strain was MG1655 Ptrc50/RBSB/TTG-icd::Cm ΔaceB Δgcl ΔglcDEFGB ΔaldA ΔiclR Δedd+eda ΔpoxB ΔackA+pta ΔmgsA ΔldhA.

Finally, the plasmid pAG25 (Example 1) was introduced into the strain MG1655 Ptrc50/RB SB/TTG-icd::Cm ΔaceB Δgcl ΔglcDEFGB ΔaldA ΔiclR Δedd+eda ΔpoxB ΔackA+pta ΔmgsA ΔldhA to give the strain MG 1655 Ptrc50/RBSB/TTG-icd::Cm ΔaceB Δgcl ΔglcDEFGB ΔaldA ΔiclR Δedd+eda ΔpoxB ΔackA+pta ΔmgsA ΔldhA (pME101-ycdW-TT07-PaceA-aceA-TT01) named AG0873.

Example 7

Construction of a Strain to Improve the Production of Glycolic Acid by Fermentation: MG1655 Ptrc50/RBSB/TTG-icd::Cm ΔaceB Δgcl ΔglcDEFGB ΔaldA ΔiclR Δedd+eda ΔpoxB ΔackA+pta ΔldhA ΔmgsA ΔarcA (pME10'-ycdW-TT07-PaceA-aceA-TT01)

The deletion ΔarcA::Km was introduced by transduction into the strain described in the Example 6, MG 1655 Ptrc50/RBSB/TTG-icd::Cm ΔaceB Δgcl ΔglcDEFGB ΔaldA ΔiclR Δedd+eda ΔpoxB ΔackA+pta ΔmgsA ΔldhA to give the strain MG1655 Ptrc50/RBSB/TTG-icd::Cm ΔaceB Δgcl ΔglcDEFGB ΔaldA ΔiclR Δedd+eda ΔpoxB ΔackA+pta ΔmgsA ΔldhA ΔarcA::Km. The donor strain MG1655 ΔarcA::Km used in the transduction experiment is described in the Example 5.

Then, the plasmid pAG25 was introduced into the strain to give the strain MG1655 Ptrc50/RBSB/TTG-icd::Cm ΔaceB Δgcl ΔglcDEFGB ΔaldA ΔiclR Δedd+eda ΔpoxB ΔackA+pta ΔmgsA ΔldhA ΔarcA::Km (pME101-ycdW-TT07-PaceA-aceA-TT01) named AG1099.

Example 8

Construction of a Strain Unable to Import Glycolate MG1655 Ptrc50/RBSB/TTG-icd::Cm ΔaceB Δgcl ΔglcDEFGB ΔaldA ΔiclR Δedd+eda ΔpoxB ΔackA+pta ΔglcA ΔlldP ΔyjcG (pME101-ycdW-TT07-PaceA-aceA-TT01)

In a first step, the construction ΔyjcG::Nm (Cre/Lox) was introduced into the strain MG1655 ΔaceB Δgcl ΔglcDEFGB ΔaldA ΔiclR Δedd+eda ΔpoxB ΔackA+pta (pKD46) by PCR product (See protocol 4) to give the strain MG1655 ΔaceB Δgcl ΔglcDEFGB ΔaldA ΔiclR Δedd+eda ΔpoxB ΔackA+pta ΔyjcG::Nm. The oligonucleotides used are shown in the table 1. The resulting strain was validated by sequencing.

The Neomycin resistance cassette was eliminated according to the technique described in protocol 5 to give the strain MG1655 ΔaceB Δgcl ΔglcDEFGB ΔaldA ΔiclR Δedd+eda ΔpoxB ΔackA+pta ΔyjcG.

In a second step, the construction ΔglcA::Nm was introduced into the strain MG1655 ΔaceB Δgcl ΔglcDEFGB ΔaldA ΔiclR Δedd+eda ΔpoxB ΔackA+pta ΔyjcG (pKD46) by PCR product (See protocol 4) to give the strain MG1655 ΔaceB Δgcl ΔglcDEFGB ΔaldA ΔiclR Δedd+eda ΔpoxB ΔackA+pta ΔyjcG ΔglcA::Nm. The oligonucleotides used are shown in the table 1. The resulting strain was validated by sequencing.

The Neomycin resistance cassette was eliminated according to the technique described in protocol 5 to give the strain MG1655 ΔaceB Δgcl ΔglcDEFGB ΔaldA ΔiclR Δedd+eda ΔpoxB ΔackA+pta ΔyjcG ΔglcA.

In a third step, the deletion ΔlldP::Km was introduced into the strain MG1655 ΔaceB Δgcl ΔglcDEFGB ΔaldA ΔiclR Δedd+eda ΔpoxB ΔackA+pta ΔyjcG ΔglcA by transduction to give the strain MG1655 ΔaceB Δgcl ΔglcDEFGB ΔaldA ΔiclR Δedd+eda ΔpoxB ΔackA+pta ΔyjcG ΔglcA ΔlldP::Km. The donor strain MG1655 ΔlldP::Km used in the transduction experiment was built by recombination of a PCR fragment introduced into an MG1655 (pKD46). The oligonucleotides are presented in table 1. The strain MG1655 ΔlldP::Km was validated by sequencing.

The next step was to transduce the attenuation Ptrc50/RBSB/TTG-icd::Cm by transduction from the strain MG1655 Ptrc50/RBSB/TTG-icd::Cm described in Example 2, into the strain MG1655 ΔaceB Δgcl ΔglcDEFGB ΔaldA ΔiclR Δedd+eda ΔpoxB ΔackA+pta ΔyjcG ΔglcA ΔlldP::Km to give the strain MG1655 Ptrc50/RBSB/TTG-icd ΔaceB Δgcl ΔglcDEFGB ΔaldA ΔiclR Δedd+eda ΔpoxB ΔackA+pta ΔyjcG ΔglcA ΔlldP::Km.

The last step was the introduction of the plasmid pAG25 (Example 1) to get the strain MG1655 Ptrc50/RBSB/TTG-icd::Cm ΔaceB Δgcl ΔglcDEFGB ΔaldA ΔiclR Δedd+eda ΔpoxB ΔackA+pta ΔyjcG ΔglcA ΔlldP (pME101-ycdW-TT07-PaceA-aceA-TT01), called AG1056.

Example 9

Construction of a Strain to Improve the Production of Glycolic Acid by Fermentation and Unable to Import Glycolate: MG1655 Ptrc50/RBSB/TTG-icd::Cm ΔaceB Δgcl ΔglcDEFGB ΔaldA ΔiclR Δedd+eda ΔpoxB ΔackA+pta ΔldhA ΔmgsA ΔglcA ΔlldP ΔyjcG (pME101-ycdW-TT07-PaceA-aceA-TT01)

In a first step, the construction ΔyjcG::Nm was introduced by PCR product (Protocol 4) into the strain MG1655 ΔaceB Δgcl ΔglcDEFGB ΔaldA ΔiclR Δedd+eda ΔpoxB ΔackA+pta ΔmgsA ΔldhA (pKD46) described in Example 6, to give the strain MG1655 ΔaceB Δgcl ΔglcDEFGB ΔaldA ΔiclR Δedd+eda ΔpoxB ΔackA+pta ΔmgsA ΔldhA ΔyjcG::Nm.

The resistance cassette was eliminated according to the protocol 5 to give the strain MG1655 ΔaceB Δgcl ΔglcDEFGB ΔaldA ΔiclR Δedd+eda ΔpoxB ΔackA+pta ΔmgsA ΔldhA ΔyjcG.

In a second step, the deletion ΔglcA::Nm (Cre/Lox) was introduced by PCR product into the strain MG1655 ΔaceB Δgcl ΔglcDEFGB ΔaldA ΔiclR Δedd+eda ΔpoxB ΔackA+pta ΔmgsA ΔldhA ΔyjcG (pKD46) to give the strain MG1655 ΔaceB Δgcl ΔglcDEFGB ΔaldA ΔiclR Δedd+eda ΔpoxB ΔackA+pta ΔmgsA ΔldhA ΔyjcG ΔglcA::Nm.

The resistance cassette was eliminated according to the protocol 5 to give the strain MG1655 ΔaceB Δgcl ΔglcDEFGB ΔaldA ΔiclR Δedd+eda ΔpoxB ΔackA+pta ΔmgsA ΔldhA ΔyjcG ΔglcA.

The third step was the introduction of ΔlldP::Km by transduction from the strain MG1655 ΔlldP::Km described in Example 8, into the strain MG1655 ΔaceB Δgcl ΔglcDEFGB ΔaldA ΔiclR Δedd+eda ΔpoxB ΔackA+pta ΔmgsA ΔldhA ΔyjcG ΔglcA to give the strain MG1655 ΔaceB Δgcl ΔglcDEFGB ΔaldA ΔiclR Δedd+eda ΔpoxB ΔackA+pta ΔmgsA ΔldhA ΔyjcG ΔglcA ΔlldP::Km.

Then the fragment Ptrc50/RBSB/TTG-icd::Cm was transduced into the strain MG1655 ΔaceB Δgcl ΔglcDEFGB ΔaldA ΔiclR Δedd+eda ΔpoxB ΔackA+pta ΔmgsA ΔldhA ΔyjcG ΔglcA ΔlldP::Km to give the strain MG 1655 Ptrc50/RBSB/TTG-icd::Cm ΔaceB Δgcl ΔglcDEFGB ΔaldA ΔiclR Δedd+eda ΔpoxB ΔackA+pta ΔmgsA ΔldhA ΔyjcG ΔglcA ΔlldP::Km. The strain MG1655 Ptrc50/RBSB/TTG-icd::Cm described in Example 2 was the donor strain for the transduction experiment.

Finally, the plasmid pAG25 was introduced into the strain by electroporation to give the strain named AG0960: MG1655 Ptrc50/RBSB/TTG-icd ΔaceB Δgcl ΔglcDEFGB ΔaldA ΔiclR Δedd+eda ΔpoxB ΔackA+pta ΔmgsA ΔldhA ΔyjcG ΔglcA ΔlldP::Km (pME10'-ycdW-TT07-PaceA-aceA-TT01)

The man skilled in the art knows the techniques used to genetically engineer a microorganism and knows that there are different ways to obtain a deletion.

Example 10

Fermentation of Glycolic Acid Producing Strains in Erlenmeyer Flasks

Performances of strains were initially assessed in 250 ml baffled Erlenmeyer flask cultures using modified M9 medium (Anderson, 1946, *Proc. Natl. Acad. Sci. USA* 32:120-128) which was supplemented with 40 g/l MOPS and 10 g/l glucose and adjusted at pH 6.8. Spectinomycin was added if necessary at a concentration of 50 mg/l. A 72 hours preculture was used to inoculate a 50 ml culture to an $OD_{600\,nm}$ of about 0.3. The cultures were kept on a shaker at 30° C. and 200 rpm until the glucose in the culture medium was exhausted. At the end of the culture, glucose and glycolic acid were analyzed by HPLC using a Biorad HPX 97H column for the separation and a refractometer for the detection.

Comparison of the performances of the different strains is given in table 3 below. The strain described in example 2 could be considered as the reference. Each value is the mean of n repetitions (n=1 to n=6).

Example 11

Fermentation of Glycolic Acid Producing Strains in Fed Batch Fermentor

The strains described in examples above were assessed under production conditions in a 600 ml fermentor using a fed batch protocol.

A unique preculture was carried out in 500 ml Erlenmeyer flask filled with 50 ml of synthetic medium supplemented with 40 g/l of MOPS, 10 g/l of glucose (the same medium used for flask cultures) and 10% of LB medium at 30° C. during 3 days. This preculture was used for inoculation of the fermentor.

The fermentor filled with 200 ml of synthetic medium supplemented with 20 g/l of glucose, 50 mg/l of spectinomycin was inoculated at an initial optical density of about 2. The culture was carried out at 37° C. with agitation and aeration adjusted to maintain the dissolved oxygen above 30% saturation. The pH was adjusted at 6.8 with base addition. The culture was conducted in a batch mode until exhaustion of glucose. At that time, a solution of 700 g/l glucose supplemented with magnesium sulfate, oligo-elements and spectinomycin was added (Pulse of glucose) to restore a concentration of 20 g/l of glucose in the medium. After the $5^{th}$ pulse of fed, the pH is adjusted at 7.4 until the end of the culture.

Routinely, strain described in example 5 gave better production performances in fermentor than the reference strain described in example 2.

A representative time-course of fermentation for production of glycolic acid using strain of example 5 (AG0956) is given below.

TABLE 5 time-course of fermentation for production of glycolic acid by the strain AG0956 in Fermentor Multifors (600 mL)

| Time (h) | $OD_{600\,nm}$ (AU) | Glucose (g/l) | Glycolic acid (g/l) |
|---|---|---|---|
| 0.0 | 1.8 | 17.4 | 0.4 |
| 15.33 | 35.3 | 12.3 | 16.9 |
| 17.83 | 49.4 | 12.7 | 23.7 |
| 20.33 | 58.6 | 11.9 | 28.9 |
| 22.83 | 63.6 | 12.4 | 33.3 |
| 25.33 | 60.4 | 12.2 | 39.7 |
| 30.92 | 58.2 | 11.0 | 47.1 |
| 39.33 | 52.0 | 0.0 | 52.2 |

The final titre obtained was 52.2 g/l glycolic acid with a yield from glucose of 0.38 g/g and a productivity of 1.33 g/l/h.

TABLE 3

Glycolic acid production performances of different strains described above

| | Strain from example n° | | | | | | | |
|---|---|---|---|---|---|---|---|---|
| | 2 | 3 | 4 | 6 | 5 | 7 | 8 | 9 |
| Name of the strain | AG0662 | AG0708 | AG0819 | AG0873 | AG0956 | AG1099 | AG1056 | AG0960 |
| Glycolic acid production (g/l) | 4.01 ± 0.3 | 4.0 ± 0.3 | 4.44 | 4.45 | 4.36 | 5.14 | 2.46 | 4.37 |
| Yield (g glycolic acid/ g glucose) | 0.38 ± 0.03 | 0.39 ± 0.04 | 0.40 | 0.43 | 0.40 ± 0.01 | 0.52 | 0.40 | 0.50 |

Citations

WO 2007/140816
WO 2007/141316
Nunez et al, (2001) Biochemistry, 354, 707-715
Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. *Escherichia coli* and *Salmonella*: Cellular and Molecular Biology. American Society for Microbiology.
WO 2008/0134051A1
US 2007/116852A1
WO 2004/033646A2
WO 2008/116852A1
Iuchi and Lin, 1988, PNAS; 85: 1888-1892
Liu and DeWulf 2004, *J Biol Chem*, 279:12588-12597
Lynch and Lin, 1996 Responses to molecular oxygen; in Neidhardt F C, Curtiss III R J, Ingraham L, Lin E C C, Low K B, Magasanik B W, Zeznikoff S, Riley M, Schaechter M, Umbarger H E (eds) *Escherichia coli* and *Salmonella*: Cellular and Molecular Biology, ed 2. Washington, American Society for Microbiology, 1996, vol 1, pp 1526-1538.
Shalel-Levanon et al., *Biotechnol. Bioeng.* 2005a; 89:556-564
Shalel-Levanon et al., *Biotechnol. Bioeng.* 2005b; 92:147-159
Aleexeva et al., 2003, *J. Bacteriol.* 185:204-209
*J. Bacteriol.* 2005, 187:3171-3179
US 2006/0073577A1
WO 2006/020663
WO 2008/116848
EP 1 382686A1
WO 2004/033646
Nunez, F. et al., 2001 *Microbiology*, 147, 1069-1077
Nunez, F. et al., 2002 *Biochem. And Biophysical research communications* 290, 824-829
Gimenez, R. et al., 2003 *J. of Bacteriol.* 185, 21, 6448-6455
Sambrook et al. (1989) Molecular Cloning: a Laboratory Manual. $2^{nd}$ ed. Cold Spring Harbor Lab., Cold Spring Harbor, N.Y.).
Carrier and Keasling (1998) *Biotechnol. Prog.* 15, 58-64
Laporte D C 1989, *Biochimie* September-October; 71(9-10):1051-7
Ikeda T P, 1992, *J Bacteriol.* February; 174(4):1414-6.
Cozzone A J, El-Mansi M. 2005, *J Mol Microbiol Biotechnol.* 9(3-4):132-46)
Georgellis et al., 1999
Iuchi, S., and Lin, E. C. C. (1993) *Mol. Microbiol.* 9, 9-15
Bauer, C. E., Elsen, S., and Bird, T. H. (1999) *Annu. Rev. Microbiol.* 53, 495-523
S. Iuchi et al., (1991) *Cell*, 66, 5-7
Jeong, J-Y. et al., 2004, *Journal of Bio. Chem*
Laub, M. T. and Goulian, M. *Annu. Rev. Genet.* (2007); 41:121-45
Datsenko, K. A. & Wanner, B. L. (2000)
Palmeros B. et al (2000), *Gene* 247: 255-264
Anderson, 1946, *Proc. Natl. Acad. Sci. USA* 32:120-128

---

The invention claimed is:

1. A method for the fermentative production of glycolic acid, its derivatives or precursors, by culturing a modified microorganism, in an appropriate culture medium comprising a source of carbon, and recovery of glycolic acid from the culture medium,
wherein said modified microorganism is a gram negative bacteria genetically modified for producing glycolic acid, that further comprises attenuation of the genes ldhA and mgsA.

2. The method according to claim 1, wherein the microorganism initially modified for producing glycolic acid comprises at least one of the following modifications:
attenuation of the conversion of glyoxylate to products other than glycolate by attenuation of aceB, glcB, gcl, eda,
is unable to substantially metabolize glycolate by attenuation of glcDEFG, aldA,
increase of the glyoxylate pathway flux by attenuation of icd, aceK, pta, ackA, poxB, iclR or fadR, and/or overexpression of aceA,
increase of the conversion of glyoxylate to glycolate by overexpression of ycdW, and/or
increase of the availability of NADPH (attenuation of pgi, udhA, edd).

3. The method according to claim 1, wherein the carbon source is at least one of the following: glucose, sucrose, mono- or oligosaccharides, starch or its derivatives or glycerol.

4. The method for the fermentative preparation of glycolate of claim 1 comprising the following steps:
a) fermentation of the modified microorganism, initially modified to produce glycolate,
b) concentration of glycolate in the bacteria or in the medium, and
c) isolation of glycolic acid from the fermentation broth and/or the biomass optionally remaining in portions or in the total amount (0-100%) in the end product.

5. The method according to claim 4, wherein glycolate is isolated through a step of polymerization to at least glycolate dimers.

6. The method according to claim 5, wherein glycolate is recovered by depolymerization from glycolate dimers, oligomers and/or polymers.

7. The method according to claim 1, wherein the modified microorganism belongs to the Enterobacteriaceae family.

8. The method according to claim 1, wherein the modified microorganism belongs to the genus *Escherichia*.

9. The method according to claim 1, wherein the modified microorganism comprises the following genetic modifications:
deletion of the genes ldhA, mgsA, aceB, gcl, glcDEFGB, aldA, iclR, edd, eda, poxB, ackA, pta;
attenuation of icd gene; and
overexpression of ycdW and aceA genes.

10. The method according to claim 1, wherein the modified microorganism comprises the following genetic modifications:
deletion of the genes arcA, aceB, gcl, glcDEFGB, aldA, iclR, edd, eda, poxB, ackA, pta;
attenuation of icd gene; and
overexpression of ycdW and aceA genes.

11. The method according to claim 1, wherein the modified microorganism comprises the following genetic modifications:
deletion of the genes glcA, lldP, yjcG, aceB, gcl, glcDEFGB, aldA, iclR, edd, eda, poxB, ackA, pta;
attenuation of icd gene; and
overexpression of ycdW and aceA genes.

12. The method according to claim 1, wherein the modified microorganism comprises the following genetic modifications:
deletion of the genes ldhA, mgsA, arcA, aceB, gcl, glcDEFGB, aldA, iclR, edd, eda, poxB, ackA, pta;
attenuation of icd gene; and
overexpression of ycdW and aceA genes.

13. The method according to claim 1, wherein the modified microorganism comprises the following genetic modifications:
deletion of the genes ldhA, mgsA, glcA, lldP, yjcG, aceB, gcl, glcDEFGB, aldA, iclR, edd, eda, poxB, ackA, pta;
attenuation of icd gene; and
overexpression of ycdW and aceA genes.

14. The method according to claim 1, wherein the microorganism initially modified for producing glycolic acid further comprises at least one of the following modifications:
attenuation of the gene arcA,
attenuation of at least one of the genes glcA, lldP, and yjcG, and combinations thereof.

15. The method according to claim 14, wherein the three genes glcA, lldP, and yjcG are attenuated.

16. A gram negative bacteria microorganism genetically modified for producing glycolic acid, that further comprises attenuation of the genes ldhA and mgsA.

17. The microorganism according to claim 16, wherein it belongs to the Enterobacteriaceae family.

18. The microorganism according to claim 17, wherein it belongs to the genus *Escherichia*.

19. The microorganism according to claim 16, further comprising at least one of the following modifications:
attenuation of the gene arcA, attenuation of at least one of the genes glcA, lldP, and yjcG, and combinations thereof.

* * * * *